US008557288B2

(12) United States Patent
Elbert et al.

(10) Patent No.: US 8,557,288 B2
(45) Date of Patent: Oct. 15, 2013

(54) HYDROGEL MICROPARTICLE FORMATION IN AQUEOUS SOLVENT FOR BIOMEDICAL APPLICATIONS

(75) Inventors: Donald L. Elbert, Clayton, MO (US); Michael D. Nichols, Durham, NC (US); Evan A. Scott, Jacksonville, FL (US)

(73) Assignee: Washington University, St. Louis, MO (US)

(*) Notice: Subject to any disclaimer, the term of this patent is extended or adjusted under 35 U.S.C. 154(b) by 582 days.

(21) Appl. No.: 12/540,937

(22) Filed: Aug. 13, 2009

(65) Prior Publication Data

US 2010/0040688 A1 Feb. 18, 2010

Related U.S. Application Data

(60) Provisional application No. 61/089,310, filed on Aug. 15, 2008.

(51) Int. Cl.
| | | |
|---|---|---|
| *A61K 9/14* | (2006.01) | |
| *A61K 39/395* | (2006.01) | |
| *A61K 38/16* | (2006.01) | |
| *A61K 38/43* | (2006.01) | |
| *A61K 38/02* | (2006.01) | |
| *A61P 41/00* | (2006.01) | |

(52) U.S. Cl.
USPC ........ 424/484; 424/78.1; 424/2.24; 424/94.1; 514/12; 514/2

(58) Field of Classification Search
USPC .................................. 424/484, 78.17; 514/12
See application file for complete search history.

(56) References Cited

U.S. PATENT DOCUMENTS

| | | | |
|---|---|---|---|
| 5,246,616 | A | 9/1993 | Bito et al. |
| 5,324,561 | A | 6/1994 | Rezai et al. |
| 5,460,817 | A | 10/1995 | Langley et al. |
| 6,271,278 | B1 | 8/2001 | Park et al. |
| 6,616,944 | B2 | 9/2003 | Kissel et al. |
| 7,276,254 | B2 | 10/2007 | Burns et al. |
| 7,347,988 | B2 | 3/2008 | Hu et al. |
| 2004/0086493 | A1 | 5/2004 | Hubbell et al. |
| 2004/0191277 | A1 | 9/2004 | Sawhney et al. |
| 2005/0008609 | A1 | 1/2005 | Cohn et al. |
| 2005/0008828 | A1 | 1/2005 | Libera et al. |
| 2006/0018948 | A1* | 1/2006 | Guire et al. ................... 424/426 |
| 2008/0063716 | A1 | 3/2008 | Moro et al. |
| 2008/0095810 | A1 | 4/2008 | Alonso et al. |

FOREIGN PATENT DOCUMENTS

| | | | | |
|---|---|---|---|---|
| WO | WO 92/20441 | * | 5/1992 | ............... B01J 13/08 |
| WO | 9220441 | A1 | 11/1992 | |
| WO | 2007103775 | A2 | 9/2007 | |
| WO | 2008142129 | A2 | 11/2008 | |

OTHER PUBLICATIONS

Groot et al. Water-soluble microgels made by radical polymerization in solution. Colloid Polym Sci 279: pp. 1219-1224 2001.*
Lutof et al. Synthesis and physicochemical characterizaiton of End-Linked Poly(ethylene glycol)-co-peptide Hydrogels Formed by Michael Tye Addition. Biomacromolecules, pp. 713-722 2003.*
Pich et al. Review Composite aqueous microgels: an overview of recent advances in synthesis, characterization, and application. Polym Int 56: 291-307 Published online Dec. 8, 2006.*
Buhler. Kollidon Polyvinlypyrrodone for the pharmaceutical industry pp. 1-288, Mar. 1998.*
Scott et al., "Modular scaffolds assembled around living cells using poly(ethylene glycol) microspheres with macroporation via a non-cytotoxic porogen," Acta Biomaterialia, vol. 6, pp. 29-38 (2010).
International Search Report and Written Opinion for PCT/US2009/053877 dated Mar. 29, 2010.
Almany et al., "Biosynthetic Hydrogel Scaffolds Made From Fibrinogen and Polyethylene Glycol for 3D Cell Cultures" Biomaterials, 26(15): 2467-2477 (2005).
Amiprour et al., "Mammalian Cell Cultures on Micropatterned Surface of Weak-Acid, Polyelectrolyte Hyperbranched Thin Films on Gold," Analytical Chemistry, 73(7): 1560-1566 (2001).
Arshady et al., "Microspheres and Microcapsules, a Survey of Manufacturing Techniques Part II: Coacervation," Polymer Engineering and Science, 30(15): 905-914 (1990).
Bailey, Jr., et al. "Some Properties of Poly(ethylene oxide) in Aqueous Solution," Journal of Applied Polymer Sci., 1(1): 56-62 (1959).
Baker et al. "Microgel, A New Macromolecule: Relation to Sol and Gel as Structural Elements of Synthetic Rubber," Industrial and Engineering Chemistry, 41(3): 511-520 (1949).
Banerjee et al., "Polymer Latexes for Cell-Resistant and Cell-Interactive Surfaces," Journal of Biomedical Materials Research, Part A, 50(3): 331-339 (2000).
Billinger et al., "Polymer Stent Coating for Prevention of Neointimal Hyperplasia," Journal of Invasive Cardiology, 18(9): 423-426, discussion 427 (2006).
Blattler et al., "High Salt Stability and Protein Resistance of Poly(L-lysine)-g-poly(ethylene glycol) Copolymers Covalently Immobilized via Aldehyde Plasma Polymer Interlayers on Inorganic and Polymeric Substrates," Langmuir, 22(13): 5760-5769 (2006).
Cai et al., "Monodisperse Thermoresponsive Microgels of Poly(ethylene glycol) Analogue-Based Biopolymers," Langmuir, 23(17): 8663-8666 (2007).
Cao et al., "Glow Discharge Plasma Treatment of Polyethylene Tubing with Tetraglyme Results in Ultralow Fibrinogen Adsorption and Greatly Reduced Platelet Adhesion," Journal of Biomedical Materials Research Part A, 79A(4): 788-803 (2006).
Carrio et al., "Preparation and Degradation of Surfactant-free PLAGA Microspheres," Journal of Controlled Release, 37(1-2): 113-121 (1995).
Chang, "Removal of Endogenous and Exogenous Toxins by a Microencapsulated Absorbent," Canadian Journal of Physiology and Pharmacology, 47(12): 1043-1045 (1969).

(Continued)

*Primary Examiner* — Anoop Singh
*Assistant Examiner* — Anna Falkowitz
(74) *Attorney, Agent, or Firm* — Armstrong Teasdale LLP

(57) ABSTRACT

The field of the disclosure relates to microparticles comprising a cross-linked water-soluble polymer or cross-linked water-soluble polymers and a process for forming thereof. Further, the field of the disclosure relates to coatings and scaffolds comprising microparticles and the processes for forming thereof.

18 Claims, 19 Drawing Sheets

(56) References Cited

OTHER PUBLICATIONS

De Feijter et al., "Ellipsometry as a Tool to Study the Adsorption Behavior of Synthetic and Biopolymers at the Air-Water Interface," Biopolymers, 17(7): 1759-1772 (1978).
De Groot et al., "Water-Soluble Microgels Made by Radical Polymerization in Solution," Colloid and Polymer Science, 279(12): 1219-1224 (2001).
Drumheller et al., "Densely Crosslinked Polymer Networks of Poly(ethylene glycol) in Trimethylolpropane Triacrylate for Cell-Adhesion-Resistant Surfaces," Journal of Biomedical Materials Research, 29(2): 207-215 (1995).
Drumheller et al., "Multifunctional poly(ethylene glycol) semi-interpenetrating polymer networks as highly selective adhesion substrates for bioadhesive peptide grafting," Biotechnology and Bioengineering, 43(8): 772-780 (1994).
Drummond et al., "Preparation of Poly(methacrylic acid-g-ethylene oxide) Microspheres," Macromolecules, 22(9): 3816-3818 (1989).
Dvir-Ginzberg et al., "Induced Differentiation and Maturation of Newborn Liver Cells into Functional Hepatic Tissue in Macroporous Alginate Scaffolds," FASEB Journal, 22(5): 1440-1449 (2008).
Eberhart et al., "Influence of Endogenous Albumin Binding on Blood-Material Interactions," Annals of the New York Academy of Sciences, Blood in Contact with Natural and Artificial Surfaces, 516(1): 78-95 (1987).
Elbert et al., "Surface Treatments of Polymers for Biocompatibility," Annual Review of Materials Science, 26: 365-394 (1996).
Elbert et al., "Conjugate Addition Reactions Combined with Free-Radical Cross-Linking for the Design of Materials for Tissue Engineering," Biomacromolecules, 2(2): 430-441 (2001).
Flory, "Molecular Size Distribution in Three Dimensional Polymers. I. Gelation," Journal of American Chemistry Society, 63(11): 3083-3090 (1941).
Flory, "Kinetics of Polyesterification: A Study of the Effects of Molecular Weight and Viscosity on Reaction Rate," Journal of the American Chemical Society, 61(12): 3334-3340 (1939).
Franssen et al., "A Novel Preparation Method for Polymeric Microparticles Without the Use of Organic Solvents," International Journal of Pharmaceutics, 168(1): 1-7 (1998).
Funke et al., "Microgels—Intramolecularly Crosslinked Macromolecules with a Globular Structure," Microencapsulation—Microgels—Iniferters, 136: 139-234 (1998).
Gan et al., "Synthesis and Protein Adsorption Resistance of PEG-Modified Poly(N-isopropylacrylamide) Core/Shell Microgels," Macromolecules, 35(26): 9634-9639 (2002).
Gasteier et al., "Surface Grafting of PEO-Based Star-Shaped Molecules for Bioanalytical Applications," Macromolecular Bioscience, 7(8): 1010-1023 (2007).
Ghosh et al, "Two New Approaches for Patterning Polymer Films Using Templates Prepared by Microcontact Printing," Macromolecules, 34(5): 1230-1236 (2001).
Graham et al., "Microgels 4: The Preparation of Novel Microgels and Their Applications," Angewandte Makromolekulare Chemie, 240(1): 113-121 (1996).
Graham et al., "Microgels Part 2. Solution Polymerization Using a Urethane Stepgrowth Mechanism," Colloids and Surfaces A: Physocochemical and Engineering Aspects, 118(3): 211-220 (1996).
Graham et al., "Nanogels and Microgels: The New Polymeric Materials Playground," Pure and Applied Chemistry, 70(6): 1271-1275 (1998).
Groll et al., "A Novel Star PEG-derived Surface Coating for Specific Cell Adhesion," Journal of Biomedical Materials Research, Part A, 74A(4): 607-617 (2005).
Groll et al., "Ultrathin Coatings from Isocyanate Terminated Star PEG Prepolymers: Patterning of Proteins on the Layers," Langmuir, 21(7): 3076-83 (2005).
Heath et al., "Varying Polymer Architecture to Deliver Drugs," AAPS Journal, 9(2):E235-E240 (2007), (http://www.aapsj.org).
Hern et al., "Incorporation of Adhesion Peptides into Nonadhesive Hydrogels Useful for Tissue Resurfacing," Journal of Biomedical Materials Research A, 39(2): 266-276 (1998).
Hill-West et al., "Inhibition of Thrombosis and Intimal Thickening by in situ Photopolymerization of Thin Hydrogel Barriers," PNAS, 91(31): 5967-5971 (1994).
Hoffmann et al., "Blood Cell and Plasma Protein Repellent Properties of Star-PEG-Modified Surfaces," Journal of Biomaterials Science, Polymer Edition, 17(9): 985-996 (2006).
Hook et al., "Variations in Coupled Water, Viscoelastic Properties, and Film Thickness of a Mefp-1 Protein Film During Adsorption and Cross-Linking: A Quartz Crystal Microbalance with Dissipation Monitoring, Ellipsometry, and Surface Plasmon Resonance Study," Analytical Chemistry, 73(24): 5796-5804 (2001).
Hyun et al., "Universal Route to Cell Micropatterning Using an Amphiphilic Comb Polymer," Advanced Materials, 15(7-8): 576-579 (2003).
Imai et al., "Biolized Materials for Cardiovascular Prosthesis," Transactions, American Society for Artificial Internal Organs, 17: 6-9 (1971).
Irvine et al., "Nanoscale Clustering of RGD Peptides at Surfaces Using Comb Polymers. 1. Synthesis and Characterization of Comb Thin Films," Biomacromolecules, 2(1): 85-94 (2001).
Jain et al., "Synthesis of Protein-Loaded Hydrogel Particles in an Aqueous Two-Phase System for Coincident Antigen and CpG Oligonucleotide Delivery to Antigen-Presenting Cells," Biomacromolecules, 6(5): 2590-2600 (2005).
Jeon et al., "Protein-Surface Interactions in the Presence of Polyethylene Oxide," Journal of Colloid and Interface Science, 142(1): 149-158 (1991).
Jeong et al., "Thermogelling Biodegradable Polymers with Hydrophilic Backbones: PEG-g-PLGA," Macromolecules, 33(22): 8317-8322 (2000).
Kawaguchi et al., "Hydrogel Microspheres III. Temperature-Dependent Adsorption of Proteins on Poly-N-Isopropylacrylamide Hydrogel Microspheres," Colloid & Polymer Science, 270(1): 53-57 (1992).
Kim et al., "Preparation and Characterization of Monodisperse Polyacrylamide Microgels," Polymer Journal, 27(5): 508-514 (1995).
Kim et al., "Thin Polymer Layers Formed Using Multi-Arm Poly(ethylene glycol) Vinylsulfone by a Covalent Layer-by-Layer Method," Biomacromolecules, 8(11): 3682-3686 (2007).
Kim et al., "Preparation and Characterization of MPEG-PCL Diblock Copolymers with Thermo-responsive sol-gel-sol Phase Transition," Journal of Polymer Science, Part A: Polymer Chemistry, 44(18): 5413-5423 (2006).
Groll et al., "Ultrathin Coatings from Isocyanate-Terminated Star PEG Prepolymers: Layer Formation and Characterization," Langmuir, 21(7): 1991-1999 (2005).
Scott et al., "Protein adsorption and cell adhesion on nanoscale bioactive coatings formed from poly(ethylene glycol) and albumin microgels," Biomaterials, 29(34): 4481-4493 (2008).
Kim et al., "Three-Dimensional Porous Biodegradable Polymeric Scaffolds Fabricated with Biodegradable Hydrogel Porogens," Tissue Engineering Part C: Methods,—Not Available—, ahead of print. doi:10.1089/ten.tec.2008.0642, 13 pages, (2009).
Kizilel et al., "Sequential Formation of Covalently Bonded Hydrogel Multilayers Through Surface Initiated Photopolymerization," Biomaterials, 27(8): 1209-1215 (2006).
Kuhl et al., "Tethered Epidermal Growth Factor as a Paradigm for Growth Factor-Induced Stimulation from the Solid Phase," Nature Medicine, 2: 1022-1027 (1996).
Lackowski et al., "Micron-Scale Patterning of Hyperbranched Polymer Films by Micro-Contact Printing," Journal of American Chemical Society, 121(6): 1419-1420 (1999).
Levesque et al., "Macroporous Interconnected Dextran Scaffolds of Controlled Porosity for Tissue-Engineering Applications," Biomaterials, 26(35): 7436-7446 (2005).
Lin et al., "In-Situ Thermoreversible Gelation of Block and Star Copolymers of Poly (ethylene glycol) and Poly(N-isopropylacrylamide) of Varying Architectures," Macromolecules, 34(11): 3710-3715 (2001).
Lopez et al., "Glow Discharge Plasma Deposition of Tetraethylene Glycol Dimethyl Ether for Fouling-Resistant Biomaterial Surfaces," Journal of Biomedical Materials Research, 26(4): 415-439 (1992).

(56) References Cited

OTHER PUBLICATIONS

Lussi et al., "Pattern Stability Under Cell Culture Conditions—A Comparative Study of Patterning Methods Based on PLL-g-PEG Background Passivation," Biomaterials, 27(12): 2534-2541 (2006).
Lutolf et al., "Repair of Bone Defects Using Synthetic Mimetics of Collagenous Extracelllular Matrices," Nature Biotechnology, 21: 513-518 (2003).
Lutolf et al., "Synthetic Matrix Metalloproteinase-Sensitive Hydrogels for the Conduction of Tissue Regeneration: Engineering Cell-Invasion Characters," Proceedings of the National Academy of Sciences USA, 100(9): 5413-5418 (2003).
Malmstrom et al., "Viscoelastic Modeling of Highly Hydrated Laminin Layers at Homogeneous and Nanostructured Surfaces: Quantification of Protein Layer Properties Using QCM-D and SPR," Langmuir, 23(19): 9760-9768 (2007).
McGuigan et al., "Vascularized Organoid Engineered by Modular Assembly Enables Blood Perfusion," Proceedings of the National Academy of Sciences, 103(31): 11461-11466 (2006).
Metters et al., "Network Formation and Degradation Behavior of Hydrogels Formed by Michael-Type Addition Reactions," Biomacromolecules, 6(1): 290-301 (2005).
Mouaziz et al., "Synthesis of Porous Microspheres via Self-Assembly of Monodisperse Polymer Nanospheres," Journal of Materials Chemistry, 14(15): 2421-2424 (2004).
Nguyen et al., "Preparation of Surfactant-Free Nanoparticles of Methacrylic Acid Copolymers Used for Film Coating," AAPS PharmSciTech, 7(3): E1-E7, Article 63, (2006), (http://www.aapspharmscitech.org).
Nolan et al., "Phase Transition Behavior, Protein Adsorption, and Cell Adhesion Resistance of Poly(ethylene glycol) Cross-Linked Microgel Particles," Biomacromolecules, 6(4): 2032-2039 (2005).
Picart et al., "Measurement of Film Thickness up to Several Hundreds of Nanometers Using Optical Waveguide Lightmode Spectroscopy," Biosensors and Bioelectronics, 20(3): 553-561 (2004).
Riccardi et al., "Surface Modification of Poly(ethylene terephthalate) Fibers Induced by Radio Frequency Air Plasma Treatment," Applied Surface Science, 211(1-4): 386-397 (2003).
Sakiyama-Elbert et al., "Development of Fibrin Derivatives for Controlled Release of Heparin-Binding Growth Factors," Journal of Controlled Release, 65(3): 389-402 (2000).
Sannino et al., "Synthesis and Characterization of Macroporous Poly(ethylene glycol)-Based Hydrogels for Tissue Engineering Application," Journal of Biomedical Materials Research Part A, 79A(2): 229-236 (2006).
Scott et al., "Nanoscopic Bioactive Coatings Formed from Poly(ethylene glycol)/albumin Microgels Greatly Reduce Protein Adsorption and Cell Adhesion," Submitted to Biomaterials on May 9, 2008, pp. 1-28.
Shen et al., "Tissue Engineering of Blood Vessels with Endothelial Cells Differentiated from Mouse Embryonic Stem Cells," Cell Research, 13(5): 335-341 (2003).
Sigma-Aldrich Co., "Microparticle Synthesis," Sigma-Aldrich, at http://www.sigmaaldrich.com/content/sigma-aldrich/areas-of-interest/life-science/cell-biology/detection/microparticles/learning-center/microparticles-synthesis.html, 3 pages, (last visited Oct. 20, 2009).
Singh et al., "Covalent Tethering of Functional Microgel Films onto Poly(ethylene terephthalate) Surfaces," Biomacromolecules, 8(10): 3271-3275 (2007).
Sodian et al., "Early in Vivo Experience with Tissue-Engineered Trileaflet Heart Valves," Circulation, 102(19 Suppl. 3): III-22 to III-29 (2000).
Stachowiak et al., "Bioactive Hydrogels with an Ordered Cellular Structure Combine Interconnected Macroporosity and Robust Mechanical Properties," Adv. Mater., 17(4): 399-403 (2005).
Stachowiak et al., "Inverse Opal Hydrogel-Collagen Composite Scaffolds as a Supportive Microenvironment for Immune Cell Migration," Journal of Biomedical Materials Research Part A, 85A(3): 815-828 (2008).
Stenekes et al., "The Preparation of Dextran Microspheres in an All-Aqueous System: Effect of the Formation Parameters on Particle Characteristics," Pharmaceutical Research, 15(4): 557-561 (1998).
Stockmayer, Theory of Molecular Size Distribution and Gel Formation in Branched-Chain Polymers, Journal of Chemical Physics, 11(2): 45-55 (1943).
Van Tomme et al., "Effect of Particle Size and Charge on the Network Properties of Microsphere-Based Hydrogels," European Journal of Pharmaceutics and Biopharmaceutics, 70(2): 522-530 (2008).
Voros, "The Density and Refractive Index of Adsorbing Protein Layers," Biophysical Journal, 87(1): 553-561 (2004).
Wacker et al., "Endothelial Cell Migration on RGD-Peptide-Containing PEG Hydrogels in the Presence of Sphingosine 1-Phosphate," Biophysical Journal, 94(1): 273-285 (2008).
Wacker et al., "Delivery of Sphingosine 1-Phosphate from Poly(ethylene glycol) Hydrogels," Biomacromolecules, 7(4): 1335-1343 (2006).
Wittmer et al., "Fibronectin Terminated Multilayer Films: Protein Adsorption and Cell Attachment Studies," Biomaterials, 28(5): 851-860 (2007).
Yeh et al., "Micromolding of Shape-Controlled, Harvestable Cell-Laden Hydrogels," Biomaterials, 27(31): 5391-5398 (2006).
Yen et al., "Fractional Precipitation of Star Poly(ethylene oxide)," Macromolecules, 29(27): 8977-8978 (1996).
Zhang et al., "Pretreatment of Amphiphilic Comb Polymer Surfaces Dramatically Affects Protein Adsorption," Macromolecules, 6(6): 3388-3396 (2005).

* cited by examiner

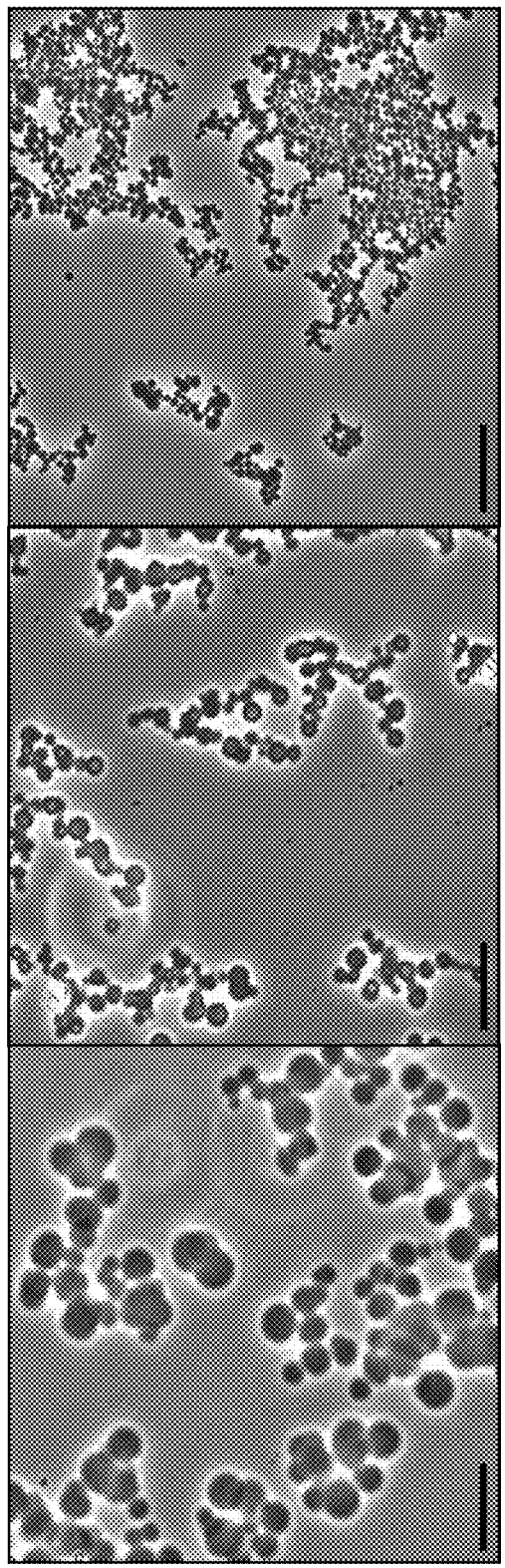

HYDROGEL MICROPARTICLE FORMATION IN AQUEOUS SOLVENT FOR BIOMEDICAL APPLICATIONS

REFERENCE TO RELATED APPLICATIONS

This application claims the benefit of U.S. Provisional Patent Application No. 61/089,310 filed Aug. 15, 2008, which is hereby incorporated by reference in its entirety.

GOVERNMENT SUPPORT

This invention was made with government support under R01HL085364 awarded by the National Institutes of Health. The government has certain rights in the invention.

BACKGROUND

Thin, biocompatible coatings for medical devices and macroporous hydrogels for tissue engineering scaffolds are ideally formed from a water-soluble polymer such as poly (ethylene glycol) (PEG). One problem with pure PEG hydrogels as scaffolds, however, is that it can be difficult for cells to infiltrate and degrade them due to their density. Macroporous hydrogels, therefore, are desirable but require incorporation of a pore-forming substance (porogen), which may be difficult to control (e.g., a foaming agent) or remove (e.g., poly (methylmethacrylate) microbeads).

PEG microparticles can suitably be formed by: (1) copolymerizing PEG with a polymer that has a lower critical solution temperature (LCST) (e.g. precipitation polymerization) or (2) using a surfactant and/or mechanical agitation to form micelles or emulsions (emulsion polymerization). Above the LCST, a solvent for a polymer becomes a non-solvent, which can cause precipitation of the polymer. A frequently used LCST polymer is poly(N-isopropylacrylamide), which allows for the production of very small spherical microparticles from a solution that would otherwise form a bulk gel. The resulting small microparticles are relatively effective as coatings for medical devices, but exhibit far from perfect biocompatibility. A potential reason for the less than ideal biocompatibility may be the presence of a large proportion of hydrophobic poly(N-isopropylacrylamide). PEG microparticles may also be formed in emulsions, e.g. water in oil, PEG/dextran in water, or PEG surfactants above the cloud point (i.e., the temperature at which dissolved solids are no longer completely soluble, precipitating as a second phase giving the fluid a cloudy appearance). The presence of these additives/non-aqueous solvents/surfactants is generally not desirable because they may be difficult to remove from the formed articles. PEG/aqueous salt solutions can be phase separated at temperatures much less than 100° C. Upon mixing, however, the stability of the phases is known to be poor, which can lead to the formation of aggregates of microparticles, which has been known to be ascribed to the low viscosity of the solution. In some instances, the presence of a surfactant has been known to be necessary in order to prevent the formation of large aggregates.

SUMMARY

In one aspect of the present disclosure, a process is disclosed for forming microparticles. The microparticles comprise a cross-linked water-soluble polymer or cross-linked water-soluble polymers. The process comprises combining monomers and/or macromers comprising at least one water-soluble polymer and at least one cross-linking agent in a solvent consisting essentially of water, wherein at least one of the monomers and/or macromers comprises a functionality of greater than 2, wherein at least one of the water-soluble polymers comprises a lower critical solution temperature (LCST), wherein functional groups of the cross-linking agent and the monomers and/or macromers react to form covalent bonds, wherein the covalent bonds form the cross-linked water-soluble polymer; and coacervation polymerizing the monomers and macromers to form a solution, wherein the coacervation polymerization comprises cross-linking the monomers and macromers at a temperature that is above the lower critical solution temperature (LCST) of at least one of the macromers, wherein the coacervation polymerization is done in the absence of mixing or agitation, wherein polymer-rich phases of the cross-linked water-soluble polymers gel before the solution coarsens to form droplets less than about 1 mm in diameter.

Another aspect of the present disclosure is directed to a process for forming a coating on a surface. The surface comprises microparticles of a cross-linked water-soluble polymer. The process comprises combining monomers and/or macromers comprising at least one water-soluble polymer and at least one cross-linking agent in a solvent consisting essentially of water, wherein at least one of the monomers and/or macromers comprises a functionality of greater than 2, wherein at least one of the water-soluble polymers comprises a lower critical solution temperature (LCST), wherein functional groups of the cross-linking agent and the monomers and/or macromers react to form covalent bonds, wherein the covalent bonds form the cross-linked water-soluble polymer; coacervation polymerizing the monomers and macromers to form a solution, wherein the coacervation polymerization comprises cross-linking the monomers and macromers at a temperature that is above the lower critical solution temperature (LCST) of at least one of the macromers, wherein the coacervation polymerization is done in the absence of mixing or agitation, wherein polymer-rich phases of the cross-linked water-soluble polymers gel before the solution coarsens to form droplets less than about 1 mm in diameter; and, forming the coating by contacting a solution of the microparticle with the surface, wherein the surface is derivatized with functional groups that react with microparticle functional groups.

Another aspect of the present disclosure is directed to a scaffold comprising hydrogel microparticles. The hydrogel microparticles are cross-linked together in the presence of living cells, wherein the cells are surrounded by the microparticles but the cells are not encapsulated in the hydrogel.

Various refinements exist of the features noted in relation to the above-mentioned aspects of the present disclosure. Further features may also be incorporated in the above-mentioned aspects of the present disclosure as well. These refinements and additional features may exist individually or in any combination. For instance, various features discussed below in relation to any of the illustrated embodiments of the present disclosure may be incorporated into any of the above-described aspects of the present disclosure, alone or in any combination.

BRIEF DESCRIPTION OF THE DRAWINGS

FIGS. 5A-5C present phase-contrast photomicrographs (20×) of microparticles produced from pre-reacted solutions of $PEG_8$-VS and $PEG_8$-amine ($d_{PCS} \cong 100$ nm) diluted to 2% (w/v) in PBS+0.6 M sodium sulfate and incubated at pH 7.4 for: (5A) 45 min at 37° C.; (5B) 10 min at 65° C.; and (5C) 5 min at 95° C. Scale bars represent 25 µm.

In FIG. 15A, a true precipitation polymerization likely leads to the monomodal distribution. In FIG. 15B, both coacervation polymerization and precipitation polymerization likely occur. The initiator is likely soluble in both polymer-rich and solvent-rich domains. In the polymer-rich domain, coacervation polymerization results. In the solvent-rich domain, the small amount of polymer still in solution undergoes a precipitation polymerization.

DETAILED DESCRIPTION

Figure 1:
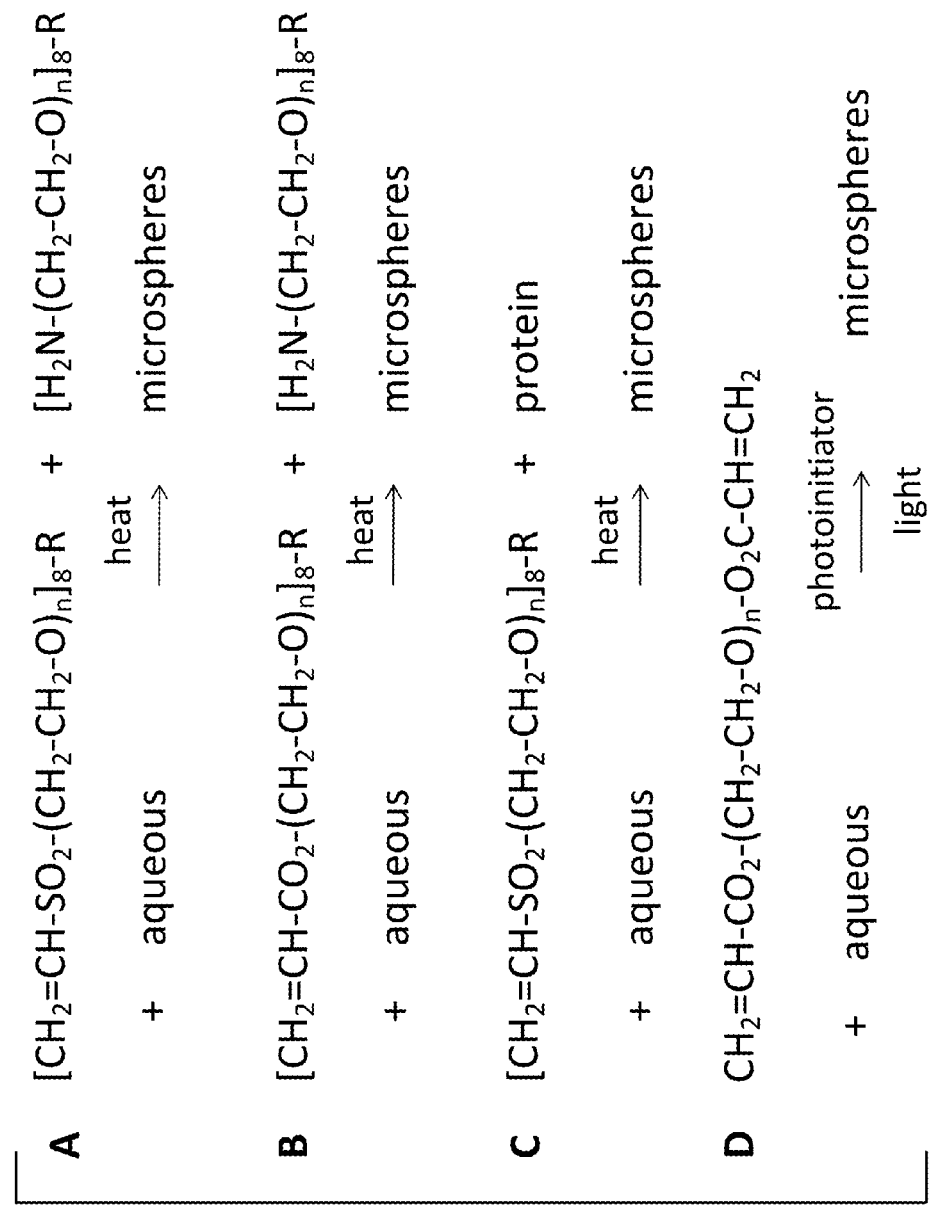
FIG. 1 presents a schematic showing of the formation of microparticles from poly(ethylene glycol)-octavinylsulfone (PEG-OVS, MW 10000) or poly(ethylene glycol)-octaacrylate (PEG-OAc, MW 10000) with poly(ethylene glycol)-octaamine (PEG-OAm, MW 10000) or protein. Vinylsulfone and acrylate groups on PEG molecules undergo a Michael-type addition with nucleophiles such as amines or thiols, forming covalent linkages at neutral pH. Proteins generally contain reactive amine groups, e.g. on the side chain of the amino acid lysine.

Exemplary embodiments of the present disclosure are directed to a process for forming microparticles. The microparticles comprise a cross-linked water-soluble polymer or cross-linked water-soluble polymers. The process comprises combining monomers and/or macromers of at least one water-soluble polymer and at least one cross-linking agent in a solvent consisting essentially of water. The monomers and/or macromers of the water-soluble polymer(s) used in the process have a functionality of greater than or equal to 2, and at least one of the polymers has a lower critical solution temperature (LCST) greater than physiological temperature (about 37° C.) in water or physiological saline, but none of the components has an LCST lower than physiological temperature in water or physiological saline. The functional groups of the cross-linking agent and monomers and/or macromers react to form covalent bonds, thereby forming the cross-linked polymer. The process comprises a coacervation polymerization of a synthetic reactive polymer, polymerizing the cross-linking polymer at a temperature that is above the LCST of the polymer whose LCST is greater than about 37° C. in water, in the absence of mechanical agitation, wherein microparticles of the cross-linked water-soluble polymer are formed. Minimization of precipitation polymerization during coacervation polymerization is also desired.

A precipitation polymerization, also known as a dispersion polymerization, is defined in some embodiments to be a polymerization in which the monomer or macromer is soluble in the solvent, but the higher molecular weight product is insoluble, hindering further crosslinking/polymerization. In another embodiment of the present disclosure, a coacervation is defined as the separation into two liquid phases in colloidal systems, wherein the phase more concentrated in colloid component is the coacervate, and the other phase is the equilibrium solution.

A coacervation polymerization is further defined in some embodiments as the crosslinking of phase separated solutions actively undergoing coarsening. Coarsening is the process by which phase separation occurs. Following a change in conditions that cause two previously soluble compounds to become insoluble, molecules aggregate into small droplets, wherein the average size of the droplets increases over time while the number of droplets decreases. Emulsion polymerization is contrasted with coacervation polymerization by the presence of an emulsifier and/or the generation of spherical domains by mixing, agitation or other mechanical means. In an emulsion polymerization, coarsening is inhibited by the emulsifier and/or counterbalanced by agitation.

Coacervation polymerizations are generally known in the field of colloid science. Gelatin, for example, may be phase separated from water at about 50° C. Before the phases completely separate, they may be stabilized by rapid cooling, causing solidification of the gelatin. For long-term stability in water of the formed gelatin microparticles, a crosslinking agent can then be introduced to the solidified gelatin.

Generally, however, the coacervation polymerization of gelatin and other colloidal proteins is a two step process (e.g., cooling then cross-linking). The process of the present disclosure, however, is a one step process (i.e., cross-linking) made possible due to fine control over the time of gelation relative to the time of phase separation. The fine control of the gelation time allows control over mean microparticle size, swelling, stiffness and buoyancy.

Another aspect of the present disclosure involves a precipitation polymerization with monomers and/or macromers of the water-soluble polymer(s) used in the process having a functionality of greater than or equal to 2, and at least one of the polymers has a lower critical solution temperature (LCST) greater than physiological temperature (about 37° C.) in water or physiological saline, but none of the components has an LCST lower than physiological temperature in water or physiological saline.

A non-cytotoxic porogen could allow the formation of a macroporous hydrogel in the presence of living cells. Furthermore, an easily degradable hydrogel could be formed if PEG microparticles were linked together with enzymatically- or hydrolytically-degradable molecules. Consequently, cells would not have to degrade the whole gel to migrate or proliferate, just the linkages between the microparticles.

It would be beneficial, then, for a better process for the production of discrete, micron or smaller sized PEG microparticles. Ideally, the process would permit the production of microparticles in aqueous solutions without the use of surfactants, emulsifiers, or other additives, wherein extensive purification of the microparticles is not needed. Furthermore, it may be beneficial to maintain reactive groups on the microparticles to allow for cross-linking of the microparticles to form coatings or scaffolds.

(I) Microparticles

One aspect of the present disclosure provides a process for forming microparticles of a cross-linked water-soluble polymer or polymers. The process comprises combining monomers and/or macromers of at least one water-soluble polymer with at least one cross-linking agent in a solvent that consists essentially of water, wherein at least one of the polymers has a lower critical solution temperature (LCST) of greater than about 37° C. in water. The mixture of monomers/macromers and cross-linking agent(s) reacts with each other to form the cross-linked polymer. The process further comprises polymerizing (e.g., coacervation polymerizing) the cross-linked polymer at a temperature that is above the LCST of the polymer whose LCST is greater than about 37° C. (in water) to form the microparticles of the cross-linked water-soluble polymer. One step in the process can be timing the gel point to occur at a time that is short relative to the complete phase separation of unstirred solutions following thermally induced phase separation. Another aspect is limiting the cross-linking of the polymer that remains in the solvent-rich phase to avoid precipitation polymerization.

Another aspect of the present disclosure is the use of a precipitation polymerization in which at least one of the polymers has a lower critical solution temperature (LCST) of greater than about 37° C. in water, but none of the components has an LCST less than 37° C. in water.

In another embodiment of the present disclosure, the macromers can be polymerized for a set period of time before heating the macromers above the LCST of the macromers.

As used herein in particular embodiments of the present disclosure, the terms "microparticle," "microsphere," "microgel," and "nanogel" are used interchangeably and refer to cross-linked polymer networks that range from about 10 nm in diameter to about 20 microns in diameter.

(I)(a) Water-Soluble Polymers

As will be appreciated by a skilled artisan, a variety of water-soluble polymers are can be used in the present disclosure. In general, the water-soluble polymer is a hydrophilic polymer. Non-limiting examples of exemplary hydrophilic polymers include, but are not limited to, polyacrylate, polyacrylamide, poly(acrylamide sulphonic acid), polyacrylonitrile, polyamines, poly(ethylene glycol), poly(ethylene imine), poly(ethylene oxide), poly(ethyloxazoline), polyhydroxyethylacrylate, polymethacrylate, polymethacrylamide, poly(oxyalkylene oxide), poly(propylene oxide), polyurethane, poly(vinyl alcohol), and poly(vinyl pyrrolidone). Preferentially, polymers with the highest second virial coefficients in water are desirable, such that they exhibit non-linear and increasing osmotic pressures as a function of concentration. Such polymers include, for example, poly(ethylene glycol) (PEG) and poly(vinyl pyrrolidone) (PVP).

At least one of the water-soluble polymers used in the process of the present disclosure will have a LCST greater than 37° C. in water. Examples of hydrophilic polymers that meet this criterion include, for example, hydroxypropylcellulose (LCST=45° C.), poly(ethyloxazoline) (LCST=60-78° C.), poly(ethylene glycol)/poly(ethylene oxide) (LCST=95-150° C.) and poly(vinyl pyrrolidone) (LCST=140-179° C.). In some embodiments, the water-soluble polymer used to make microparticles of cross-linked polymer may be poly (ethylene glycol) or poly(vinyl pyrrolidone).

The monomers and/or macromers of the water-soluble polymers will generally have a functionality of greater than or equal to 2. For example, the monomers/macromers may have a functionality of 3, 4, 5, 6, 7, 8, 9, 10, and so forth. Functionality may be due to the presence of an unsaturated bond or the presence of a functional end-group. Exemplary functional end-groups include sulfones, sulfoxides, sulfonates, sulfonamides, sulfhydryls, phosphonates, phosphonamides, acrylates, amines, alkynes, azides, isocyanates, halides, hydroxyls, carboxyls, and esters. Exemplary functional groups include vinylsulfone, amine, and acrylate.

The monomers and/or macromers of the water-soluble polymer will generally be branched, i.e., have a plurality of arms. In some embodiments, the monomers and/or macromers may be multi-armed. For example, in some embodiments, the polymer may be poly(ethylene glycol), which has four-arms (i.e., PEG-tetra). In another embodiment, the polymer may be poly(ethylene glycol), which has six-arms. In yet another embodiment, the polymer may be poly(ethylene glycol), which has eight arms (i.e., PEG-octa).

Similarly, each arm comprising a polymer, such as the poly(ethylene glycol), may have a different molecular weight. In some embodiments, each arm of the water-soluble polymer may have an average molecular weight of from about 200 daltons to about 35,000 daltons. In another embodiment, each arm of the water-soluble polymer may have an average molecular weight of from about 15,000 daltons to about 35,000 daltons. In yet another embodiment, each arm of the water-soluble polymer may have an average molecular weight of from about 2,000 daltons to about 15,000 daltons. In a further embodiment, each arm of the water-soluble polymer may have an average molecular weight of from about 200 daltons to about 2,000 daltons.

In some embodiments, exemplary monomers and/or macromers for use in the process of making microparticles include PEG-octavinylsulfone (PEG-OVS), PEG-octaamine (PEG-OAm), PEG-tetraacrylate (PEG-TAc) and PEG-octaacrylate (PEG-OAc).

In another embodiment of the present disclosure, the macromers and/or monomers comprise greater than about 75% by weight poly(ethylene glycol) or poly(vinyl pyrrolidone).

(I)(b) Cross-Linking Agents

The cross-linking agent (or agents) used to make the microparticles of a cross-linked polymer may be a small molecule (such as, e.g., dithiothreitol), a peptide, a protein, a linker molecule, a biomolecule, or monomers/macromers of a water-soluble polymer. Non-limiting examples of peptides, proteins, or biomolecules that may be used as cross-linkers include, but are not limited to, lipid-binding proteins (e.g., bovine serum albumin (BSA), lipoproteins (e.g., high density lipoproteins such as Apo A-I, Apo B-48, or Apo B-100), RGD peptides, protease-degradable peptide linkers, heparin-binding proteins, growth factors, fusion proteins (e.g., proteins containing glutathione S-transferase (GST) tags, FLAG tags, or biotin tags), enzymes (e.g., sphingosine kinase), and antibodies. Cross-linking agents may be used to subsequently include therapeutic molecules in the microparticles via affinity interactions. The affinity interactions may be mediated by antigen-antibody interactions, biotin-avidin interactions, small molecule-protein interactions, and the like. Exemplary therapeutic molecules include pharmaceutically active agents, heparin, glutathione, lipids, growth factors, and other bioactive agents.

In some embodiments of the present disclosure, the affinity interaction is mediated by antibodies, heparin or heparin-binding peptides. In another embodiment, the active agent is a lipid and the binding is to a lipid-binding protein.

The cross-linking agent suitably has a functionality of greater than 2. In some embodiments, the water-soluble polymers themselves may be considered a cross-linking agent if they have a functionality greater than 2. The cross-linking agent may have functional groups selected from the group consisting of sulfones, sulfoxides, sulfonates, sulfonamides, sulfhydryls, phosphonates, phosphonamides, acrylates, amines, alkynes, azides, isocyanates, halides, hydroxyls, carboxyls, and esters. Those of skill in the art will appreciate that the functional groups of the cross-linking agent will be complementary to the functional groups of the polymer monomers/macromers detailed above in section (I)(a).

(I)(c) Forming Microparticles

The process of the present disclosure comprises combining monomers/macromers from section (I)(a) with cross-linking agent(s) from section (I)(b). The combination of monomers/macromers and cross-linking agent(s) can vary (see, e.g., FIG. 1). In some embodiments, PEG-OVS may be combined with BSA. In another embodiment, PEG-OVS may be combined with PEG-OAm. In yet another embodiment, PEG-OAc or PEG-TAc may be combined with PEG-OAm. The ratio of functional groups of the monomers/macromers to the functional groups of the cross-linking agent(s) may range from about 1:0.2 to about 1:4.

The monomers/macromers and cross-linking agent(s) are combined in a solvent consisting essentially of water. That is, in some embodiments of the present disclosure, the solvent is devoid of surfactants, dispersants, emulsifiers, phase separation agents, and organic solvents. For example, the process can be substantially free of a surfactant or a solvent other than water. The solvent may further comprise salts (i.e. ions). For example, the aqueous solvent may comprise physiological concentrations of salts (e.g., 130-150 mM of sodium/potassium chloride). The salts may be in a polymer form, e.g. a polyelectrolyte (e.g. poly(acrylic acid)). The solvent may further comprise water-miscible solvents such as alcohols that affect the phase behavior of the reactive polymer. The solvent may further comprise other uncharged polymers or osmolytes (e.g. dextran or glycerol) that affect the phase behavior of the reactive polymer.

The complementary functional groups of the monomers/macromers and cross-linking agent(s) react to form covalent bonds, thereby forming the cross-linked polymer. In some embodiments, the polymerization is a condensation polymerization. The bonds formed between the monomers/macromers and cross-linking agent(s) may be essentially non-degradable or they may by degradable. In some embodiments, the bonds may be degradable by hydrolysis. For example, the ester linkages between PEG-OAm and PEG-TAc or PEG-OAc may be hydrolyzed in water within two days under physiological conditions. In another embodiment, the bonds may be enzymatically degradable. The bonds may be degraded by proteases, such as matrix metalloproteinases, or other enzymes. The microparticles formed by the process generally comprise unreacted functional groups that may be used in downstream applications (e.g., making coatings or scaffolds).

During the polymerization process, the molecular weight of the cross-linked polymers increases until one molecule grows to fill a portion of the volume of the original solvent. Thus, during the course of the cross-linking process, a distribution of larger and larger cross-linked polymers may be found. In particular, dynamic light scattering may be used to reveal the presence of large polymers prior to the gel point (i.e., the point at which an infinite polymer network first appears). Dynamic light scattering, thus, may be useful in determining how close to the gel point the reaction has proceeded.

The process can further comprise phase separating the partially cross-linked polymer solutions as a coacervate by adjusting the temperature of the reaction such that it is above the LCST of the polymer whose LCST is greater than 37° C. (in water). The time it takes to reach the gel point may be decreased by increasing the temperature. The cross-linking reaction may be allowed to proceed at one temperature below the cloud point for a period of time, or until a certain average size of cross-linked polymers is reached, as judged by light scattering. For example, the cross-linking reaction may be allowed to proceed at about 37° C. for several hours (i.e., about 3-5 hrs) to many hours (i.e., about 18-24 hrs). However, it is also possible to mix the monomers/macromers and cross-linking agent(s) and then immediately heat the mixture to above the LCST of the polymer whose LCST is greater than 37° C. (in water). In both cases, the cross-linked polymers that are detectable by light scattering will generally be present prior to phase separation or microparticle formation, as the cross-linking reaction may proceed at some rate between the time the reactive polymers are mixed and the time at which phase separation occurs. Thus, the time remaining until the gel point is reached generally will depend on the temperature history. Even if the components are mixed and the mixture is immediately heated above the LCST, it still may take a certain period of time before the mixture actually heats up to the target temperature, and since the elevated temperature will increase the rate of the reaction, the reaction will possibly reach an advanced degree of cross-linking before the LCST is crossed.

The pH may also affect the speed of reaction. Thus, the cross-linking reaction may be allowed to proceed for shorter times or longer times at a pH different from physiological pH (pH=7.4), particularly if one of the components contains pH-sensitive reactive groups. For example, PEG microparticles formed at pH 5.0 are larger in size than PEG microparticles formed at pH 8.0 if formed using PEG-amine. The pH of the coacervation reaction may range from about pH 3 to about pH 10, or more preferably from about pH 5 to about pH 8. One factor in the process is thus the ability to predict and/or measure and thus control the time remaining until gelation.

While mixing may hasten phase separation, some small amount of mixing prior to gelation may be used to produce larger microparticles. The reacting components could be phase separated individually and then mixed, but the mixing step will affect coarsening and thus microparticle size. In one emulsion process known in the art, the solutions were allowed to substantially phase separate and then were vigorously agitated in an attempt to produce spherical droplets. With PEG and magnesium sulfate, this produced large aggregates of microparticles following free radical polymerization. Stirring was thus unable to prevent coarsening on the time scale of cross-linking. This was attributed to the low viscosity of the solution, which potentially led to rapid coarsening. This illustrates that the kinetics of cross-linking should be well matched to the kinetics of coarsening. If the amount of mixing or agitation of the solution leads to an acceptable increase in the coarsening rate, mixing and agitation may also be used in the process. However, to prevent aggregation of particles, one can halt mixing prior to reaching the gel point.

In another embodiment of the present disclosure, increasing the ionic strength of the aqueous solvent may decrease the LCST. Ionic strength may be adjusted by the addition of sodium sulfate, sodium phosphate, magnesium sulfate, potassium sulfate, potassium chloride, potassium bromide, and the like. That is, in some embodiments, the LCST is decreased by increasing a concentration of ions in the solvent. The concentration of ions may be added during combination of the macromers and/or monomers in a sufficient amount to decrease the LCST. The concentration of additional ions may be at least about 300 mM, at least about 400 mM, at least about 500 mM, or at least about 600 mM. As shown in the examples, 600 mM sodium sulfate reduces the LCST of PEG to less than 37° C. Additionally, temperatures much higher than the LCST may be utilized, reducing the duration of time required to produce microparticles. For example, 100° C. for 10 min can be sufficient for PEG microparticle formation in the presence of 600 mM sodium sulfate (see the examples). In general, the higher the temperature, the shorter the time until microparticle formation is complete.

Ionic strength can affect the rate of coarsening in that higher salt concentration can lead to a greater difference in the densities of the two phases. The phases more rapidly separate due to the large density difference, requiring a faster rate of reaction. Thus, an optimal range of salt concentrations may exist. An exemplary salt concentration is 0.6 M sodium sulfate in PBS for coacervation polymerization of PEG-OVS and PEG-OAm. At this salt concentration, the solution is not phase separated at room temperature, allowing mixing of the components without affecting coarsening. However, the solution becomes phase separated at 37° C. Other PEG derivatives will have different LCST behavior and will have different optimal salt concentrations. For a precipitation polymerization, 0.54 M sodium sulfate in PBS is desirable. At this salt concentration, PEG-diacrylate is soluble during photoinitiated free radical polymerization at room temperature. However, the polymerized product is not water-soluble at this salt concentration, limiting the size of polymerized domains.

The distance between the cross-links can generally affect the mechanical properties of a microparticle. The distance between cross-links may be adjusted by using polymers of different molecular weights. The distance between cross-links may also be varied by halting the reaction before complete cross-linking. As a result, microparticles may be formed that vary in stiffness. This may be useful in producing homogenous materials with specific mechanical properties or permeability to solutes, or in forming materials with gradients in mechanical properties or permeability.

Although the polymer solutions are phase separated, some amount of polymer typically remains in the solvent-rich phase. This can be a hindrance to a successful free-radical polymerization. If the initiator is soluble in the solvent-rich phase, the polymer remaining in the solvent-rich phase can tend to polymerize. This may lead to a precipitation polymerization as the molecular weight of the macromer increases. Polymerization within the polymer-rich phase may also occur, leading to a bimodal distribution of sizes (see, e.g., FIGS. 15A and 15B). By lowering the salt concentration slightly, however, the macromer may be made soluble throughout the polyermization process. Only a true precipitation polymerization occurs, which can result in a monomodal distribution of microparticle sizes.

(II) Scaffolds

Another aspect of the present disclosure is directed to a scaffold comprising hydrogel microparticles, wherein the hydrogel microparticles are cross-linked together in the presence of living cells, wherein the cells are surrounded by the microparticles but the cells are not encapsulated in the hydrogel.

Scaffolds for supporting cell growth are generally known in the art, including two types of microengineered scaffolds: top down and bottom up. Top down scaffolds start with a bulk hydrogel that is made non-homogenous by a variety of patterning methods. Bottom up scaffolds can be produced by assembling cell-laden hydrogel microparticles. Microengineered scaffolds are described herein that have favorable properties of both types of scaffolds but fit into neither category.

Some embodiments of the present disclosure provide a process for forming a scaffold for tissue engineering, wherein the scaffold comprises microparticles of a cross-linked water-soluble polymer. The process comprises contacting a solution of at least one type of microparticle formed by the method of the present disclosure with an optional cross-linking agent, wherein the functional groups of the microparticles and the optional cross-linking agent(s) react to form the scaffold. In some embodiments, the solution can be a dilute solution. In another embodiment of the present disclosure, some of the microparticles may dissolve over time and if the degradation products are non-cytotoxic, a macroporous, cell-laden scaffold may result.

The microparticles used in making the scaffold are described above in section (I). Exemplary examples of cross-linking agents are detailed above in section (I)(b), and include small molecules (such as dithiothreitol), peptides, and proteins. However, the novelty of the method is not limited to the microparticles of section (I).

The process comprises contacting a solution of microparticles and an optional cross-linking agent, wherein the functional groups of the microparticles react with each other or with the optional cross-linking agent to form the scaffold. Different types of microparticles may be combined to form scaffolds with specific properties. Furthermore, different types of microparticles may be combined with different types of cross-linking agents to afford scaffolds with different properties. A variety of biomolecules may be incorporated into the scaffold by interactions with the microparticles or cross-linking agents (as detailed section (I)(b) and the examples). Cells may be seeded in the scaffolds or the scaffolds may be formed in the presence of living cells. In some embodiments, the microparticles are mixed with living cells before cross-linking. The thickness and shape of the scaffold can vary depending upon the intended use of the scaffold.

Scaffolds may be formed at the same time as microparticles are formed, provided they are given enough time to come in contact and react. Alternatively, a time for microparticle formation may be chosen so that microparticles exist primarily as isolated particles or aggregates of less than about 10 microparticles. Then, different types of microparticles may be mixed and used to form a scaffold, imparting properties of each of the types of microparticle on the scaffold as a whole. The microparticles may also be linked together in a scaffold in a way that introduces a gradient in some property, which may be advantageous in directing cell, tissue or blood vessel responses to the material. Thus, a highly modular approach to scaffold formation is possible.

Scaffolds may comprise microparticles formed with degradable covalent bonds. In some embodiments of the present disclosure, the scaffold comprises microparticles formed with degradable covalent bonds and microparticles formed with substantially non-degradable covalent bonds. Further, in another embodiment, the scaffold may comprise microparticles comprising a non-covalently conjugated therapeutic molecule. The therapeutic molecule may be included in the microparticles via affinity interactions. The therapeutic molecule can be selected from the group consisting of a small molecule, a pharmaceutically active agent, a lipid, a peptide, a protein, an enzyme, a growth factor, and an antibody.

Scaffolds may be formed by cross-linking the microparticles in a variety of ways. With PEG-OVS/PEG-OAm based microparticles, free functional groups are generally present after microparticle formation. These same groups may be used to cross-link microparticles into scaffolds. Simple centrifugation or settling generally can be sufficient to produce a scaffold. If the microparticle density is lower than the solution density, floating of the microparticles to the top can be sufficient for scaffold formation.

Alternatively, a cross-linking agent such as dithiothreitol may be used to cross-link the microparticles to form a scaffold. Other cross-linking agents include peptides, proteins or polymers that contain multiple functional groups, e.g., thiols or amines. If the microparticles are cross-linked into a scaffold using a peptide that is enzymatically degradable, the scaffold may be returned to the microparticle form by the action of an enzyme. If the enzymes are secreted by migrating cells, the degradation of the scaffolds by the cells may lead to faster migration than if the cells had to degrade a homogenous gel. Proteins also may be used to cross-link the microparticles into scaffolds and the proteins themselves may be enzymatically degradable.

Proteins and peptides may also be added to the scaffolds, which may impart biological activity but not necessarily enhance scaffold formation. Proteins and peptides that enhance scaffold formation may also be chosen to impart biological activity in the scaffolds. Examples include cell adhesion peptides, growth factors, and antibodies, particularly antibodies directed against stem cells or progenitor cells. By incorporating glutathione into the microparticles, the scaffolds may also trap proteins containing a GST tag, including enzymes that produce bioactive lipids such as a sphingosine kinase-GST fusion protein.

In some embodiments of the present disclosure, glutathione is covalently linked to a subset of microparticles. In another embodiment, an active enzyme is bound to the glutathione. In another embodiment, the active enzyme is a sphigosine kinase.

In some embodiments of the present disclosure, mixing microparticles that do not readily degrade in water with microparticles that rapidly degrade by water hydrolysis followed by cross-linking to form scaffolds may lead to the formation of highly porous scaffolds following dissolution of the degradable microparticles. In some embodiments of the present disclosure, the scaffold is formed with bonds degradable by hydrolysis. In another embodiment, the scaffold is formed from microparticles formed with bonds degradable by hydrolysis and microparticles formed with bonds not substantially degradable in water and the resulting porous construct.

Microparticles formed by the process of the present disclosure may also be mixed with microparticles made by known processes prior to scaffold formation. For example, poly(lactic/glycolic) acid microparticles containing growth factors may be incorporated in the scaffold.

Scaffold formation is modular with regard to the different types of microparticles that may be mixed to form the scaffolds. The mixture of microparticles does not need to be homogenous and, consequently, scaffolds comprising gradients of different microparticles may be formed. Gradients may be introduced using differences in microparticle density, which can be accomplished by incubating microparticles for different lengths of time above the cloud point. Gradients may also be introduced by modifying the net charge on different microparticles and using electrophoresis to separate the microparticles. Gradients may also be introduced using a gradient mixer containing different types of microparticles in the different reservoirs of the gradient mixer. Gradients may be formed by other means, for example, by gently layering solutions containing different microparticles on top of each other.

In some embodiments, the scaffold may provide a generic three-dimensional tissue culture system. Scaffolds may be formed and then seeded with cells or implanted for cell in-growth. Scaffolds may be formed from a variety of particles to introduce macropores or biological functionalities that encourage cell in-growth and angiogenesis. These properties may be present in the form of gradients of microparticle types. Cells may be mixed with the microparticles prior to cross-linking. Non-limiting examples of exemplary cells include fibroblasts, epithelial cells, blood cells, precursor blood cells, immune system cells, hepatocytes, renal cells, chondrocytes, osteoblasts, respiratory tract cells, gut cells, bladder cells, pancreatic cells, myoblasts, skeletal muscle cells, heart muscle cells, smooth muscle cells, exocrine gland cells, hormone secreting cells, sensory transducer cells, neurons, neuron supporting cells, and stem cells. If the scaffolds rapidly promote the in-growth of blood vessels due to delivery of angiogenic agents, cell survival may enhance the formation of functional tissues. Rapid ingrowth of nerves may enhance physiological control of the new tissue.

(III) Coatings

Another aspect of the present disclosure is directed to a process for forming a coating on a surface, wherein the surface comprises microparticles of a cross-linked water-soluble polymer. The process comprises combining monomers and/or macromers comprising at least one water-soluble polymer and at least one cross-linking agent in a solvent consisting essentially of water, wherein at least one of the monomers and/or macromers comprises a functionality of greater than 2, wherein at least one of the water-soluble polymers comprises a lower critical solution temperature (LCST), wherein functional groups of the cross-linking agent and the monomers and/or macromers react to form covalent bonds, wherein the covalent bonds form the cross-linked water-soluble polymer; coacervation polymerizing the monomers and macromers to form a solution, wherein the coacervation polymerization comprises cross-linking the monomers and macromers at a temperature that is above the lower critical solution temperature (LCST) of at least one of the macromers, wherein the coacervation polymerization is done in the absence of mixing or agitation, wherein polymer-rich phases of the cross-linked water-soluble polymers gel before the solution coarsens to form droplets less than about 1 mm in diameter; and forming the coating by contacting a solution of the microparticle with the surface, wherein the surface is derivatized with functional groups that react with microparticle functional groups.

The microparticles used in making the coating are described above in section (I). Different microparticles may provide different properties, such as mechanical support, porosity (via degradable linkages), pH-responsiveness, or delivery of therapeutic molecules. The therapeutic molecule within the microparticle can comprise a non-covalently conjugated therapeutic molecule. The therapeutic molecule can be selected from the group consisting of a small molecule, a pharmaceutically active agent, a lipid, a peptide, a protein, an enzyme, a growth factor and an antibody. Furthermore, the coatings may be made even omitting the phase separation step, e.g. with the pre-reacted macromer solutions themselves.

In general, the surface to be coated is derivatized with functional groups that are complementary to the functional groups of the microparticles. For example, the surface may be contacted with mercaptopropyltrimethoxysilane (MPTS) to provide thiol functional groups. Alternatively, the surface may be contacted with 3-aminopropyltriethoxysilane to provide amine functional groups on the surface. Those of skill in the art will be familiar with other exemplary derivatizing reagents.

The method comprises contacting the surface to be coated with a solution of microparticles, wherein the functional groups of the microparticles react with the functional groups on the surface to form the coating. Different types of microparticles may be combined to form coatings with specific properties. In some embodiments, the solution is a dilute solution.

The surface to be coated may be glass, plastic, or metal. Exemplary surfaces include silver, gold, stainless steel, titanium, glass, silicon, cadmium, palladium, platinum, iron, nickel, cobalt, iron oxide, titanium oxide, silicon oxide, and copper. The surface to be coated may be the surface of a medical device. Exemplary medical devices include cardiovascular devices, such as vascular grafts and stents, artificial blood vessels, artificial bone joints, such as hip joints, and scaffolds that support tissue growth in such anatomical structures as nerves, pancreas, eye and muscle. Other exemplary medical devices include biosensors and percutaneous devices, such as catheters, that penetrate the skin and link a living body to a medical device, such as a kidney dialysis machine. The coating may also be applied to contact lenses, intraocular lenses, ultrafiltration membranes, and containers for biological materials. Additionally, cell culture dishes, or portions thereof, may be coated to minimize adhesion of cells to the dish. Cell culture dishes treated in this manner only allow cell spreading in those areas which are not treated, when the cells are anchorage dependent cells, they must be anchored to a solid support in order to spread. The coating may be applied to the treatment of macrocapsular surfaces, such as those used for ultrafiltration, hemodialysis, and non-microencapsulated immunoisolation of animal tissue. The surface to be coated may be in the form of a hollow fiber, a spiral module, a flat sheet, or other configuration. The surface may be a material used for an in vitro diagnostic assay.

The surface to be coated may be dipped into a solution of microparticles, or the solution of microparticles may be spread on the surface, sprayed on the surface, or any other method known in the art. The thickness of the coating can vary depending upon the downstream application of the surface. In general, the thickness of the coating will be less than about 10 microns. In some embodiments, the thickness of the coating may be about 75 nm. In a further embodiment, more than one layer of coating may be applied to the surface such that the coating may comprise 2 or more distinctly formed layers. The number of distinctly formed layers may range form about two to about 100, or more preferably from about five to about 20 distinctly formed layers.

Advantageously, the coating made by the process of the present disclosure can be protein rejecting and resists cell adhesion. As detailed below, proteins and cells do not generally substantially adhere to coatings made by the process detailed here. In some embodiments, the coating is from about 90 percent to about 99 percent protein rejecting. In another embodiment, the coating is at least about 95 percent protein rejecting. In yet another embodiment the coating is at least about 99 percent protein rejecting.

In yet another embodiment of the present disclosure, a surface coating is formed by combining macromers and/or monomers of at least one water-soluble polymer and at least one cross-linking agent in a solvent consisting essentially of water, at least some of the monomers and/or macromers having a functionality of greater than 2; and, contacting the solution with a surface modified with at least one type of functional group having a greater reactivity than the functional groups on the monomer and/or macromer.

In alternative embodiments of the present disclosure, the process for forming a coating comprises polymerizing the solution until the solution contains detectable microparticles that are greater than about 10 nm in diameter instead of the coacervation polymerization step.

The following examples illustrate various embodiments of the present disclosure.

EXAMPLES

Example 1

Pre-Reaction of PEG-OVS/PEG-OAm

PEG-OVS/PEG-OAm microparticle containing solutions with mean effective diameters of approximately 100 nm as measured by dynamic light scattering (DLS) were synthesized by combining 200 mg/mL solutions of PEG-OA and PEG-OVS in Dulbecco's modified phosphate-buffered saline (DPBS; 8 mM sodium phosphate, 2 mM potassium phosphate, 140 mM sodium chloride, 10 mM potassium chloride) pH 7.4 in a 1:1 ratio by volume (final concentrations of 100 mg/mL for each reagent) and incubating this mixture at 37° C. while rotating at 40 RPM for approximately 4-5 h.

Example 2

Pre-Reaction of PEG-TAc/PEG-OAm and PEG-OAc/PEG-Oam

PEG-TAc/PEG-OAm microparticle solutions with mean effective diameters of approximately 100 nm as measured by DLS were synthesized by combining 200 mg/mL solutions of PEG-TAc and PEG-OAm in DPBS, pH 7.4 in a 2:1 ratio of PEG-TAc:PEG-OA by volume (final concentrations of 133.33 mg/mL PEG-TAc and 66.67 mg/mL PEG-OAm) and incubating this mixture at 37° C. while rotating at 40 RPM for approximately 18 h. PEG-OAc and PEG-OAm solutions at 200 mg/mL in DPBS, pH 7.4 in a 1:1 ratio of PEG-OAc and PEG-OAm were incubated at 37° C. while rotating at 40 RPM to a $d_{PCS}$ of 100 nm within about 7 h.

Example 3

Pre-Reaction of PEG-OVS/BSA

PEG-OVS/BSA microparticle solutions with mean effective diameters of approximately 100 nm as measured by DLS were synthesized by combining 200 mg/mL solutions of fatty acid free (FAF) BSA and PEG-OVS in DPBS, pH 7.4 in a 3:2 ratio of BSA:PEG-OVS by volume (final concentrations of 120 mg/mL BSA and 80 mg/mL PEG-OVS) and incubating this mixture at 37° C. while rotating at 40 RPM for approximately 7-8 h.

Example 4

Formation of Microparticles from Pre-Reacted PEG-OVS/PEG-OAm in Sodium Phosphate or Sodium Sulfate at pH 5.0 Over 10 Min VS-OAm microparticles were fabricated in 1.5 mL centrifuge tubes by diluting PEG-OVS/PEG-OAm pre-reacted solutions 10× (final concentrations of 10 mg/mL for each reagent) with 1.5 M sodium phosphate or sodium sulfate at pH 5.0 and deionized water such that the final concentration of sodium phosphate was 500 mM, mixing well, and then incubating these for 10 min at 100° C. in a heating block without agitation.

Example 5

Formation of Microparticles from Pre-Reacted PEG-OVS/PEG-OAm in Sodium Sulfate at pH 6.5 or pH 7.4

Figures 2A, 2B:
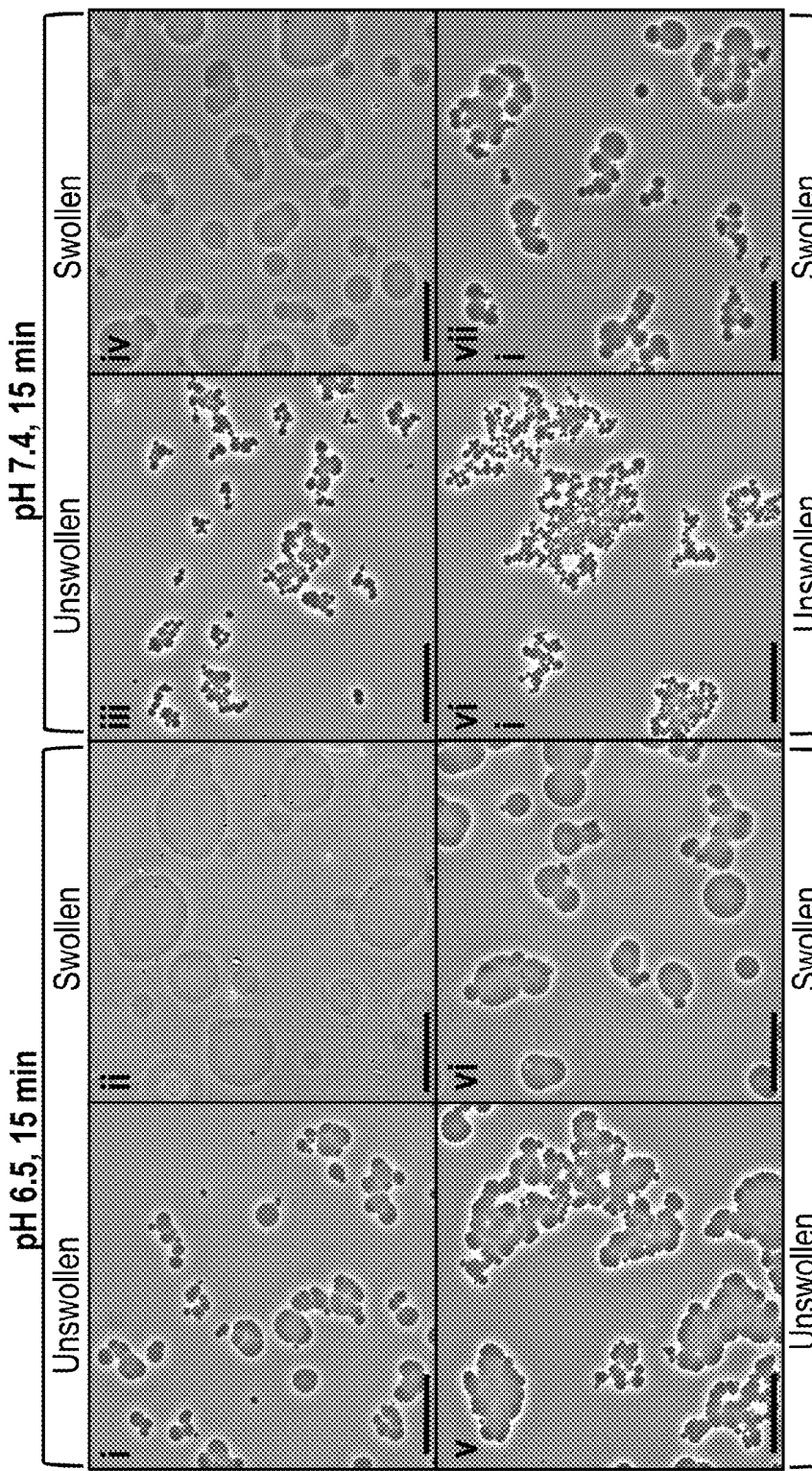
FIGS. 2A and 2B present phase-contrast photomicrographs (20×) of OVS-OAm microparticles demonstrating the swelling of microparticles following buffer exchange into phosphate-buffered saline (PBS). All microparticles were formed from pre-reacted solutions ($d_{PCS} \cong 100$ nm) diluted to 2% (w/v) in PBS with 600 mM sodium sulfate and incubated at 37° C. for: (i) 15 min at pH 6.5 without buffer exchange (ii) 15 min at pH 6.5 with buffer exchange (iii) 15 min at pH 7.4 without buffer exchange (iv) 15 min at pH 7.4 with buffer exchange (v) 105 min at pH 6.5 without buffer exchange (vi) 105 min at pH 6.5 with buffer exchange (vii) 75 min at pH 7.4 without buffer exchange (viii) 75 min at pH 7.4 with buffer exchange. Scale bars represent 25 µm. As can be seen from the Figures, the size of the microparticles increase as the pH decreases.

VS-OAm microparticles were fabricated in 1.5 mL centrifuge tubes by diluting PEG-OVS/PEG-OAm pre-reacted solutions 10× (final concentrations of 10 mg/mL for each reagent) with 1.5 M sodium sulfate at pH 6.5 or pH 7.4 and DPBS such that the final concentration of sodium sulfate was 600 mM, mixing well, and then incubating these for 15, 75 or 105 min at 37° C. in a heating block without agitation (see, e.g., FIGS. 2A and 2B).

Example 6

Figure 3:
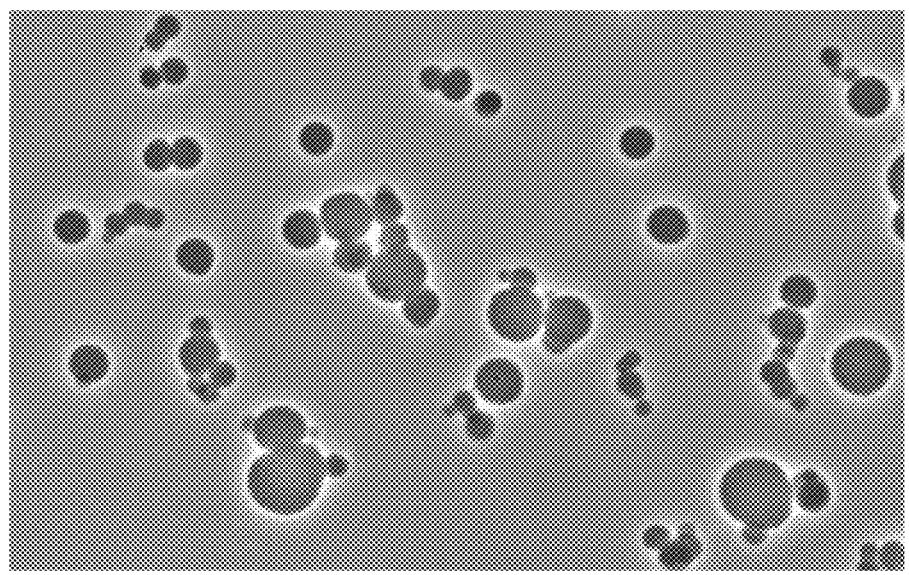
FIG. 3 presents a phase-contrast photomicrograph (20×) of OVS-OAm microparticles fabricated in 600 mM sodium sulfate in DPBS at pH 7.4 over 45 min at 37° C. Formed microparticles were buffer exchanged into PBS.

Formation of Microparticles from Pre-Reacted PEG-OVS/PEG-OAm in Sodium Sulfate in DPBS at pH 7.4 Over 45 Min VS-OAm microparticles were fabricated in 1.5 mL centrifuge tubes by diluting PEG-OVS/PEG-OAm pre-reacted solutions 10× (final concentrations of 10 mg/mL for each reagent) with 1.5 M sodium sulfate in DPBS at pH 7.4 and DPBS alone such that the final concentration of sodium sulfate was 600 mM, mixing well, and then incubating these for 45 min at 37° C. in a heating block without agitation (see FIG. 3).

Figure 4A:
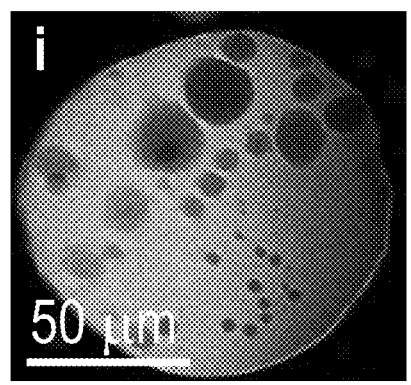
FIGS. 4A and 4B present confocal microscopy of porous microparticles formed above the cloud point. Water-rich droplets were observed within OVS-OAm microparticles that formed in PBS+0.8 M sodium sulfate, phase-separated at room temperature for 5 min and heated at 37° C. for 15 min: (i-ii) progression of coarsening of water-rich domains within PEG-rich droplets over 15 min.
Figure 4B:
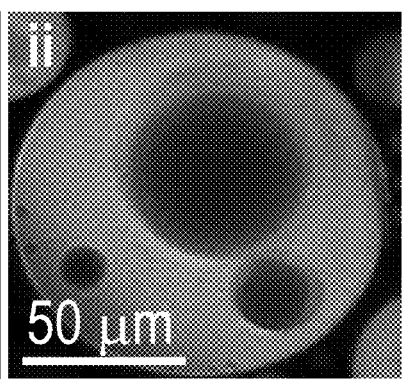

To observe the structure of the microparticles, PEG-OVS/PEG-OAm pre-reacted solutions 10× (final concentrations of 10 mg/mL for each reagent) with 1.5 M sodium sulfate in DPBS at pH 7.4 and DPBS alone such that the final concentration of sodium sulfate was 800 mM, mixing well. The solution polymer phase separated during mixing at room temperature, was held at room temperature for 5 min, and then incubated for 15 min at 37° C. in a heating block without agitation (see, e.g., FIGS. 4A and 4B). This resulted in the formation of larger microparticles, presumably larger due to enhanced coarsening caused by mixing.

Example 7

Formation of Microparticles from Pre-Reacted PEG-OAc/PEG-OAm in Sodium Sulfate in DPBS at pH 7.4 Over 10 Min OAc-OAm microparticles were fabricated in 1.5 mL centrifuge tubes by diluting PEG-OAc/PEG-OAm pre-reacted solutions 10× (1:1 acrylate:amine; final concentrations of 10 mg/mL for each reagent) with 1.5 M sodium sulfate in DPBS at pH 7.4 and DPBS alone such that the final concentration of sodium sulfate was 450 mM, mixing well, and then incubating these for 10 min at 95° C. in a heating block without agitation.

Example 8

Formation of Microparticles from Pre-Reacted PEG-OVS/BSA in Sodium Sulfate in DPBS at pH 7.4 Over 20 Min VS-BSA microparticles were fabricated in 1.5 mL centrifuge tubes by diluting PEG-OVS/BSA pre-reacted solutions 10× (2:1 VS:amine; final concentrations of 85 mg/mL BSA and 115 mg/mL PEG-OVS) with 1.5 M sodium sulfate in DPBS at pH 7.4 and DPBS alone such that the final concentration of sodium sulfate was 650 mM, mixing well, and then incubating 20 min at 37° C. in a heating block without agitation.

Example 9

Length of Incubation Above the Cloud Point and Temperature Affect Microparticle Size $PEG_8$-VS and $PEG_8$-amine microparticles were formed as in Example 6 but were incubated for 45 min at 37° C., 10 min at 65° C., or 5 min at 95° C. in a heating block without agitation (see, e.g., FIGS. 5A-5C).

Figure 6:
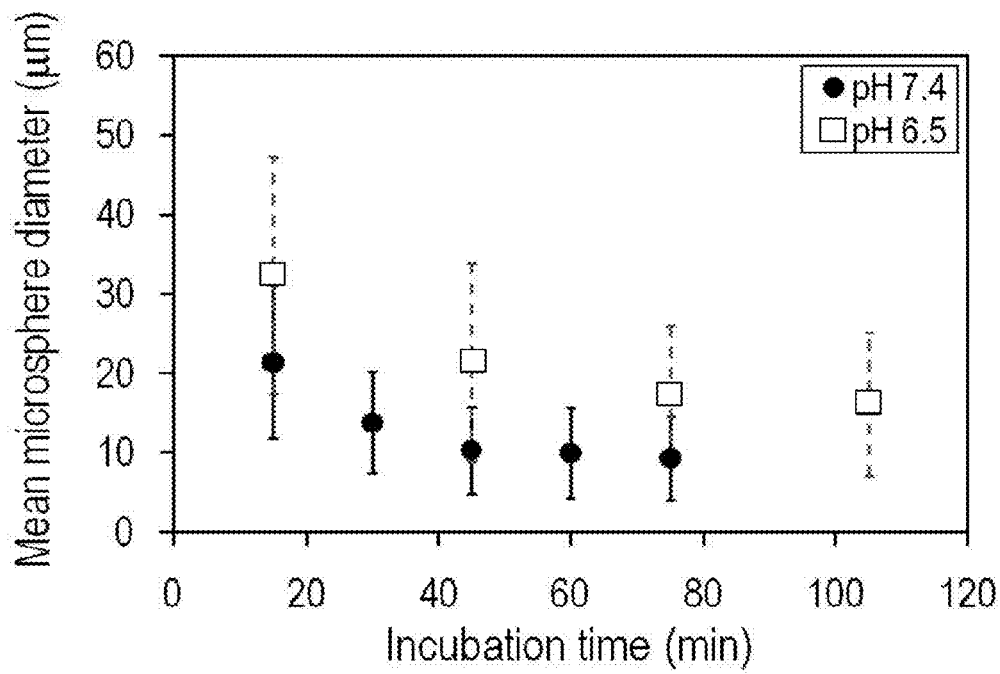
FIG. 6 presents the effects of reaction duration on the sizes of swollen microparticles. Unless otherwise stated, microparticles were formed from pre-reacted solutions of $PEG_8$-VS and $PEG_8$-amine ($d_{PCS} \cong 100$ nm) diluted to 2% (w/v) in PBS+0.6 M sodium sulfate, incubated at 37° C. for 45 min, and buffer exchanged into PBS. Microparticle diameters decreased with increasing incubation time above the cloud point, with pH 6.5 microparticles approaching but not matching pH 7.4 sizes even at extended timepoints. For pH 6.5 reactions, PEG solutions were pre-reacted to $d_{PCS} \cong 150$ nm to allow multiple observations prior to microparticle aggregation/bulk gel formation. Data represent n=500 microparticles at each timepoint. *p<0.05 versus the 105 min timepoint for pH 6.5 and #p<0.05 versus the 75 min timepoint for pH 7.4. No significant changes in size were observed after 75 min at pH 6.5 or after 45 min at pH 7.4. Data represent n=500 microparticles at each pH. *p<0.05 versus all other pHs and p<0.05 versus pH 6.0-7.4.

$PEG_8$-VS and $PEG_8$-amine microparticles were formed as in Example 6 at either pH 7.4 or pH 6.5 for 15-105 min at 37° C. and buffer exchanged into PBS. Microparticle diameters were measured manually after phase contrast microscopy for n=500 microparticles at each timepoint (see FIG. 6).

Figure 7:
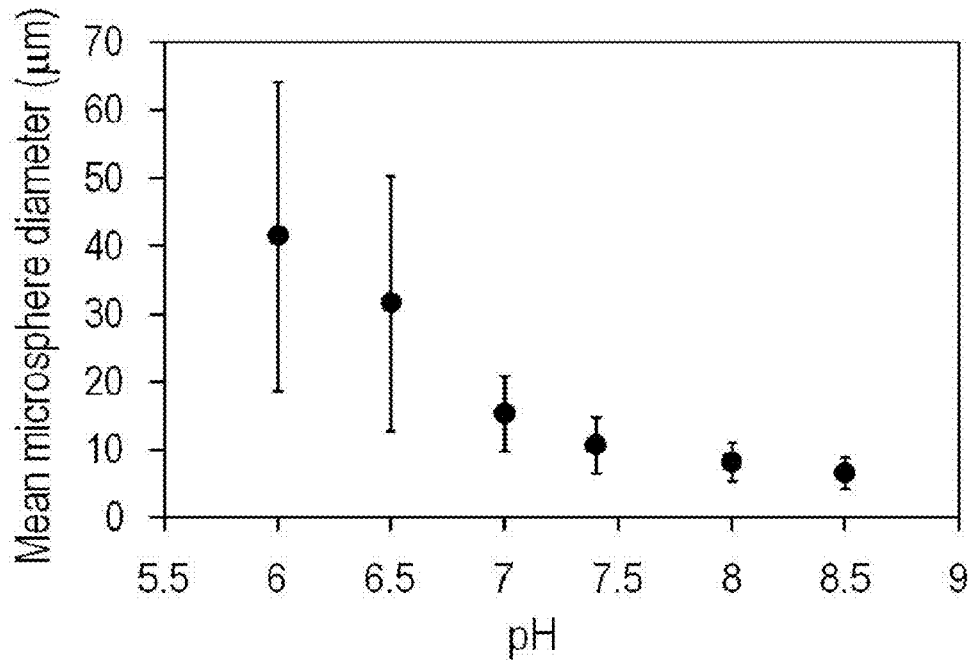
FIG. 7 presents the effects of pH on the sizes of swollen microparticles. Microparticle diameters and polydispersity indices (PDIs) were observed to decrease with increasing pH. Data represent n=500 microparticles at each pH. *p<0.05 versus all other pHs and #p<0.05 versus pH 6.0-7.4.
Figure 8:
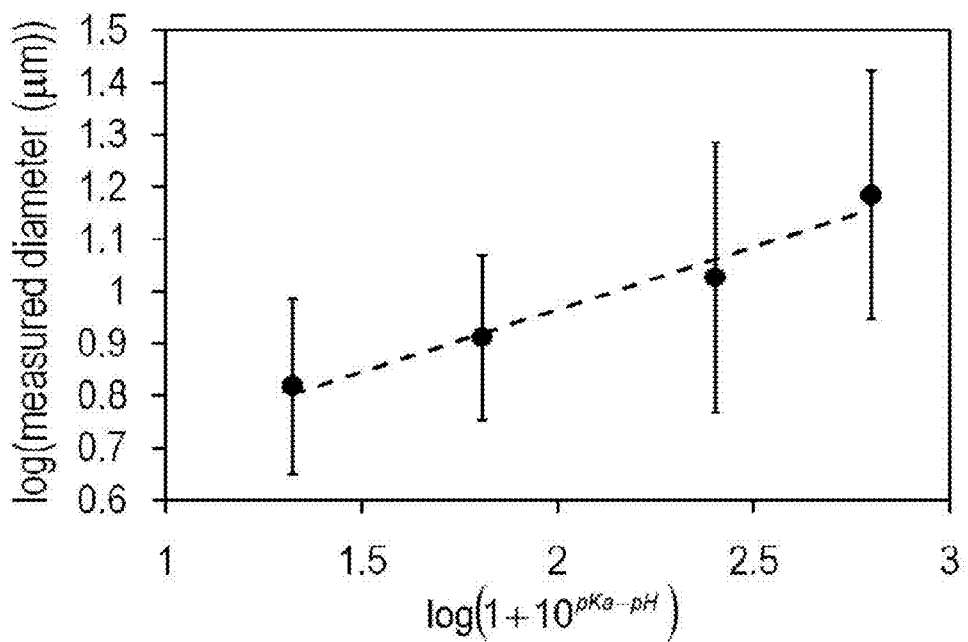
FIG. 8 presents power law plots of mean microparticle diameter versus normalized time remaining to the gel point based on the degree of pre-reaction using the data in FIG. 2B. Linear regression yielded slopes equal to 0.24. The expected value for coarsening by Ostwald ripening and/or coalescence is ⅓, corresponding to an $R \propto time^{1/2}$ growth law, where R is the mean radius of the phase-separated domains. Standard deviations were calculated by propagation of error.

Example 10 pH and Length of Pre-Reaction Affect Size of Microparticles $PEG_8$-VS and $PEG_8$-amine microparticles were formed as in Example 6 at pH 6-8.5 for 45 min at 37° C. and buffer exchanged into PBS. Microparticle diameters were measured manually after phase contrast microscopy for n=500 microparticles at each timepoint (see FIGS. 7 and 8).

Figure 9:
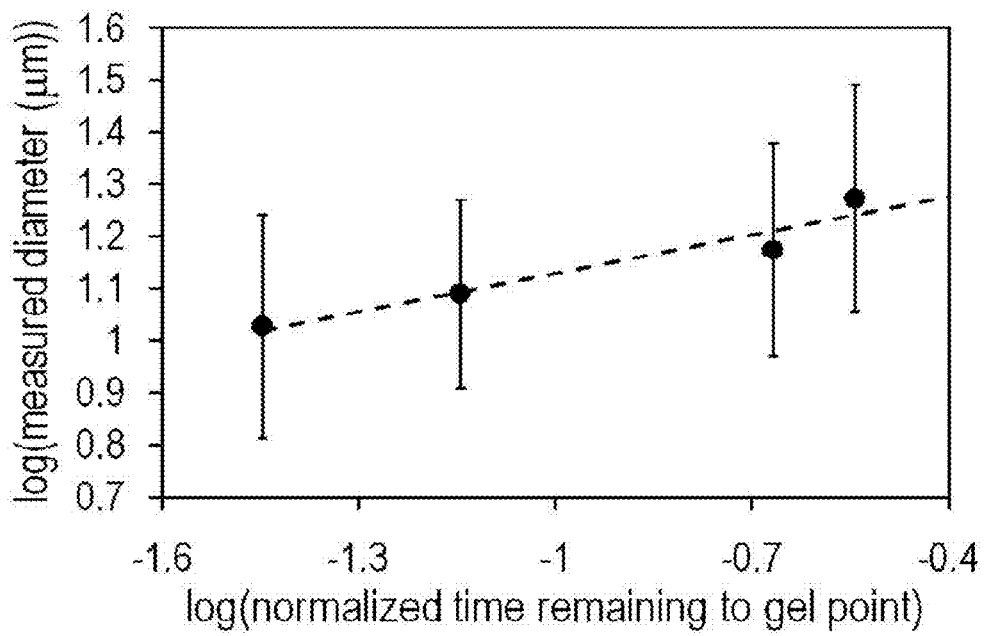
FIG. 9 presents power law plots of mean microparticle diameter versus the pH-dependent amine reactivity using the data from FIG. 2B. Linear regression yielded slopes equal to 0.24. The expected value for coarsening by Ostwald ripening and/or coalescence is ⅓, corresponding to an $R \propto time^{1/2}$ growth law, where R is the mean radius of the phase-separated domains. Standard deviations were calculated by propagation of error.

$PEG_8$-VS and $PEG_8$-amine were pre-reacted to dPCS of 43.2, 58.3, 115.4, or 162.6 nm. The pre-reacted solutions were then reacted as in Example 6. Microparticle diameters were measured manually after phase contrast microscopy for n=500 microparticles at each timepoint (see FIG. 9).

Example 11

Scaffold Formation from PEG-OVS/PEG-OAm Microparticles Without Additional Cross-Linker VS-OAm microparticles were fabricated as in Example 6. After buffer exchange, this solution of microparticles was centrifuged at 14,100 g for 2 min and then incubated overnight at 37° C. to afford a scaffold.

Example 12

Non-Controllably Degradable Scaffold Formation from PEG-OVS/PEG-OAm Microparticles with a Small Molecule VS-OAm microparticles were fabricated as in Example 6. This solution of microparticles was buffer-exchanged twice by: (1) adding triple the volume of DPBS of the microparticle solution and pipetting up and down to mix well, (2) centrifuging at 14.1 g for 2 min, (3) removing the supernatant, and (4) repeating steps 1-3. The pellet of microparticles resulting from the second buffer exchange was resuspended in a 1 mM solution of dithiothreitol (DTT) cross-linker in DPBS whose volume was approximately double the combined volume of the pellet and residual supernatant. The microparticles in cross-linker solution was gently shaken for 2 h in a temperature-controlled room at 37° C., centrifuged at 14,100 g for 2 min, and then incubated at 37° C. in a heating block overnight to afford a scaffold.

Example 13

Enzymatically Degradable Scaffold Formation from PEG-OVS/PEG-OAm Microparticles with a Small Molecule VS-OAm microparticles were fabricated as in Example 6. This solution of microparticles was buffer-exchanged twice by: (1) adding triple the volume of DPBS of the microparticle solution and pipetting up and down to mix well, (2) centrifuging at 14,100 g for 2 min, (3) removing the supernatant, and (4) repeating steps 1-3. The pellet of microparticles resulting from the second buffer exchange was resuspended in a 1 mM solution of a matrix metalloproteinase (MMP)-degradable peptide cross-linker (sequence=Ac-GCRD-GPQG ↓ IWGD-DRCG; SEQ ID NO: 1) in DPBS whose volume was approximately double the combined volume of the pellet and residual supernatant.

The resuspended microparticles were gently shaken for 2 h in a temperature-controlled room at 37° C., centrifuged at 14,100 g for 2 min, and then incubated at 37° C. in a heating block overnight to afford a scaffold.

Example 14

Scaffold Formation from PEG-OVS/PEG-OAm Microparticles with Protein Cross-Linker VS-OAm microparticles were fabricated as in Example 6. This solution of microparticles is buffer-exchanged twice by: (1) adding triple the volume of DPBS of the microparticle solution and pipetting up and down to mix well, (2) centrifuging at 14,100 g for 2 min, (3) removing the supernatant, and (4) repeating steps 1-3. The pellet of microparticles resulting from the second buffer exchange is resuspended in a 1 mM solution of fatty acid free bovine serum albumin (FAF-BSA) DPBS whose volume is approximately double the combined volume of the pellet and residual supernatant. The resuspended microparticles are gently shaken for 2 h in a temperature-controlled room at 37° C., centrifuged at 14,100 g, and then incubated at 37° C. in a heating block overnight to afford a scaffold.

Example 15

Non-Controllably Degradable Porous Scaffold Formation from Small Molecule Cross-Linking PEG-OVS/PEG-OAm and PEG-TAc/PEG-OAm Microparticle TA-OAm and VS-OAm microparticles were fabricated as detailed in Example 2 and in Example 6, respectively.

Both solutions of microparticles were buffer-exchanged twice by: (1) adding triple the volume of DPBS of each microparticle solution and pipetting up and down to mix well, (2) centrifuging at 14,100 g for 2 min, (3) removing the supernatant, and (4) repeating steps 1-3. Each pellet of microparticles resulting from the second buffer exchange was resuspended in a 1 mM solution of dithiothreitol (DTT) in DPBS whose volume was approximately double the combined volume of the pellet and residual supernatant.

These microparticle solutions were then consolidated into a single centrifuge tube and gently shaken for 2 h in a temperature-controlled room at 37° C., centrifuged at 100 g for 5 min, and then incubated at 37° C. in a heating block overnight to afford a scaffold. TAc-OAm microparticles can then be dissolved (i.e., made porous) by raising the pH or by heating (continued incubation at 37° C. for two days).

Example 16

Enzymatically Degradable Porous Scaffold Formation from Small Molecule Cross-Linking PEG-OVS/PEG-OAm and PEG-TAc/PEG-OAm Microparticles TAc-OAm and VS-OAm microparticles were fabricated as detailed in Example 15.

Both solutions of microparticles are buffer-exchanged twice by: (1) adding triple the volume of DPBS of each microparticle solution and pipetting up and down to mix well, (2) centrifuging at 14,100 g for 2 min, (3) removing the supernatant, and (4) repeating steps 1-3. Each pellet of microparticles resulting from the second buffer exchange is resuspended in a 1 mM solution of the matrix metalloproteinase (MMP)-degradable peptide cross-linker in DPBS whose volume is approximately double the combined volume of the pellet and residual supernatant.

These microparticle solutions are then consolidated into a single centrifuge tube and gently shaken for 2 h in a temperature-controlled room at 37° C., centrifuged at 100 g for 5 min, and then incubated at 37° C. in a heating block overnight to afford a scaffold. TAc-OAm microparticles can then be dissolved by raising the pH or by heating (continued incubation at 37° C. for two days).

Example 17

Non-Controllably Degradable Porous Scaffold Formation from Protein Cross-Linking PEG-OVS/PEG-OAm and PEG-OAc/PEG-OAm Microparticles OAc-OAm and VS-OAm microparticles were fabricated as in Example 7 and Example 6, respectively.

Both solutions of microparticles are buffer-exchanged twice by: (1) adding triple the volume of DPBS of each microparticle solution and pipetting up and down to mix well, (2) centrifuging at 14,100 g for 2 min, (3) removing the supernatant, and (4) repeating steps 1-3. Each pellet of microparticles resulting from the second buffer exchange was resuspended in a 1 mM solution of fatty acid free bovine serum albumin (FAF-BSA) in DPBS whose volume was approximately double the combined volume of the pellet and residual supernatant.

These microparticle solutions were then consolidated into a single centrifuge tube and centrifuged at 1000 g for 10 min, and then incubated at 37° C. in an incubator overnight to afford a scaffold. OAc-OAm microparticles were dissolved by continued incubation at 37° C. for 2 days.

Example 18

Scaffold from Cross-Linking PEG-OVS/PEG-OAm Microparticles Incorporating Covalently Coupled RGD Peptide PEG-OVS/PEG-OAm were pre-reacted as detailed In Example 6, but with 2:1 PEG-OVS:PEG-OAm and reacted to $d_{PCS}$=50 nm before addition of 5.5 mM RGD peptide (Am-GCGYGRGDSPG) for 30 min.

Figure 10:
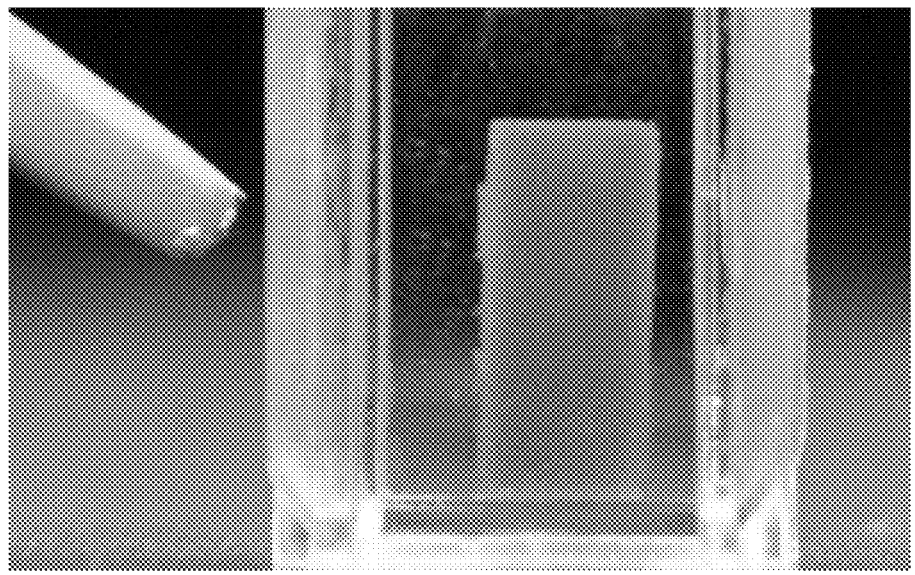
FIG. 10 presents a photograph of a scaffold composed of OVS-OAm microparticles, OAc-OAm microparticles and OVS-BSA microparticles. Microparticles were compacted by centrifugation at 1000 g for 10 min in the presence of HepG2 hepatoma cells and then incubated for 12 h at 37° C. in medium with 2% FBS.
Figure 11:
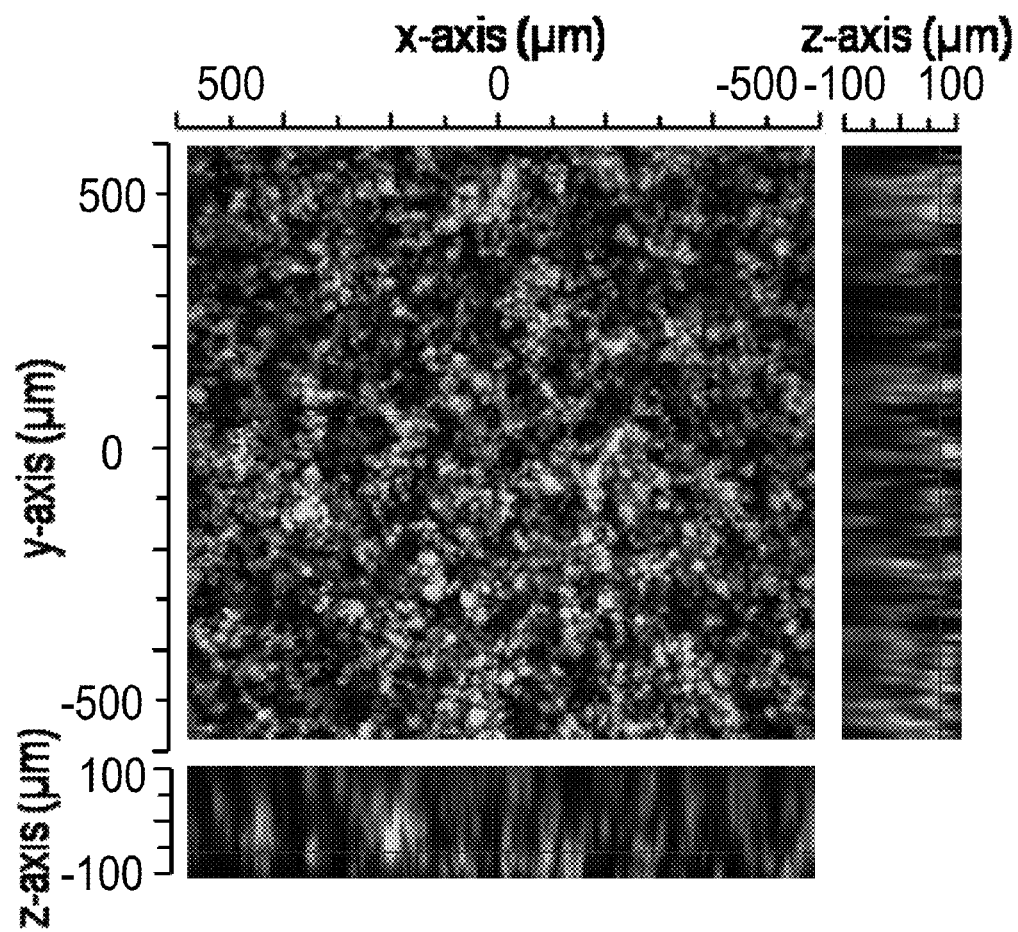
FIG. 11 presents confocal microscopy of macroporous scaffold composed of PEG-OVS/PEG-OAm microparticles, OAc-OAm microparticles OVS-BSA microparticles, 48 h after formation. Microparticle densities were matched to produce an even distribution of macropores (black) following dissolution of OAc-OAm microparticles.
Figure 12:
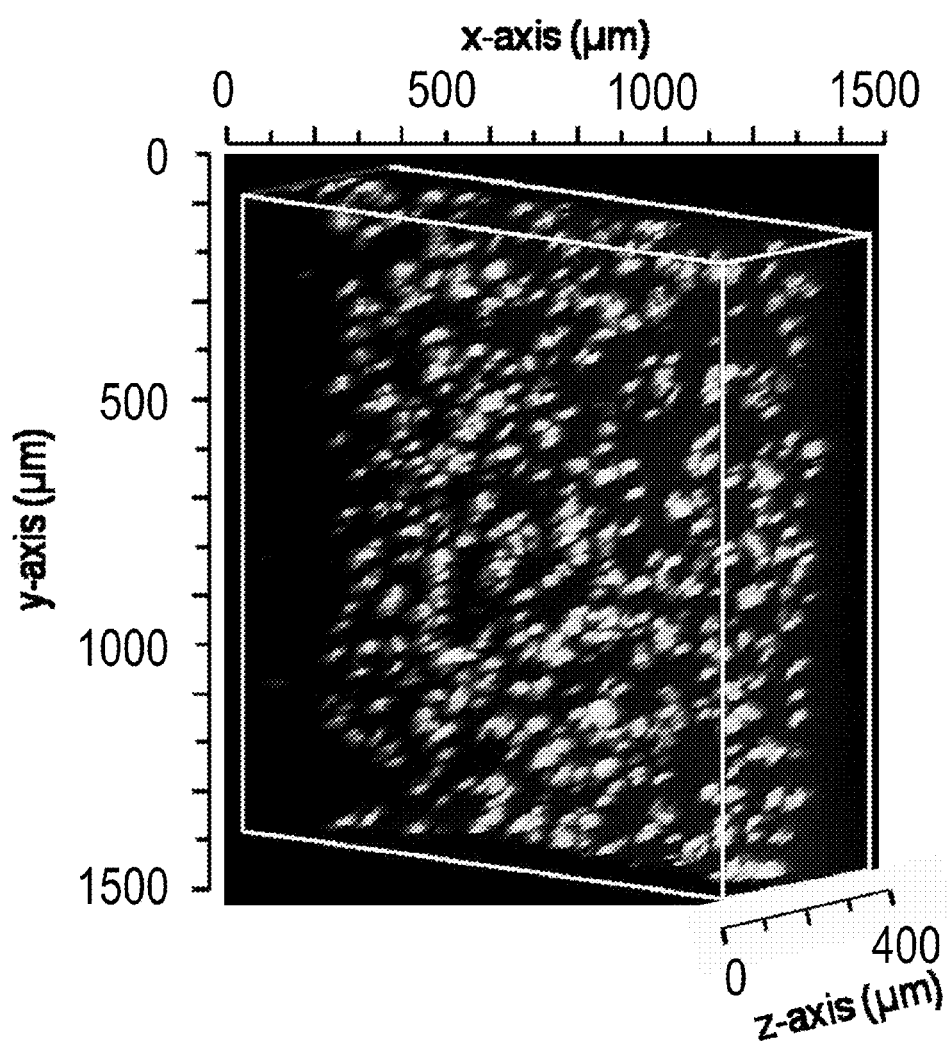
FIG. 12 presents a live/dead assay of HepG2 cells within a scaffold composed of OVS-OAm microparticles, OAc-OAm microparticles, and OVS-BSA microparticles. The cell-laden scaffold was formed by centrifuging a suspension of microparticles and cells within media containing 2% serum. After 48 h of incubation at 37° C., the OAc-OAm microparticles were no longer detectable, demonstrating complete hydrolysis of porogenic microparticles. Live HepG2 cells were stained with fluorescein diacetate (white) and demonstrated 91.94±1.87% cell viability.

Microparticles are fabricated in 1.5 mL centrifuge tubes by first diluting the pre-reacted solution 10× (final concentrations of 10 mg/mL for each reagent) with 1.5 M sodium sulfate in DPBS at pH 7.4 and DPBS alone to achieve 0.6 M sodium sulfate. This solution was then mixed well and incubated for 45 min at 37° C. to afford microparticles. The microparticles were buffer exchanged into PBS and mixed OAc-OAm and VS-BSA microparticles reacted with RGD peptide as above, in a volume ratio of 1:1:1. The microparticles were also mixed with HepG2 cells in medium with 2% serum and centrifuged at 1000 g for 10 min. Further incubation overnight at 37° C. produced scaffolds (see FIGS. 10 & 11). Cell viability was 93.64±3.34%. After two days, pores had formed due to dissolution of OAc-OAm microparticles, with cell viability of 91.94±1.87% (see FIG. 12).

Example 19

Scaffold from Cross-Linking PEG-OVS/PEG-OAm Microparticles Incorporating Covalently Coupled Growth Factors VS-OAm microparticles are fabricated as detailed in example 6.

This solution of microparticles is buffer-exchanged twice by: (1) adding triple the volume of DPBS of the microparticle solution and pipetting up and down to mix well, (2) centrifuging at 14,100 g for 2 min, (3) removing the supernatant, and (4) repeating steps 1-3. The pellet of microparticles resulting from the second buffer exchange is resuspended in a 1 mM solution of vascular endothelial growth factor (VEGF) in DPBS whose volume is approximately equal to the combined volume of the pellet and residual supernatant.

The resuspended microparticles are gently shaken for 2 h in a temperature-controlled room at 37° C., centrifuged at 1000 g, and then incubated at 37° C. in a heating block overnight to afford a scaffold.

Example 20

Scaffold from Cross-Linking PEG-OVS/PEG-OAm Microparticles Incorporating Covalently Coupled Antibodies VS-OAm microparticles are fabricated as detailed in Example 6.

This solution of microparticles is buffer-exchanged twice by: (1) adding triple the volume of DPBS of the microparticle solution and pipetting up and down to mix well, (2) centrifuging at 14,100 g for 2 min, (3) removing the supernatant, and (4) repeating steps 1-3. The pellet of microparticles resulting from the second buffer exchange is resuspended in a 0.1 mM solution of generic Fc receptor for IgG (IgG FcR) in DPBS whose volume is approximately equal to the combined volume of the pellet and residual supernatant. The resuspended microparticles are gently shaken for 2 h in a temperature-controlled room at 37° C., centrifuged at 100 g, then buffer-exchanged twice again as in steps 1-4 above but centrifuging at 100 g for 5 min instead of 14.1 g for 2 min. The pellet of microparticles is then incubated at 37° C. in a heating block overnight to afford a scaffold.

As much excess DPBS hydrating the IgG FcR-coupled scaffold as possible is removed, and an approximately equal volume of 0.25 M anti-CD34 monoclonal antibody (α-CD34 mAb) in DPBS is added. The scaffold is incubated in this solution for 4 h at 37° C. in a heating block to allow α-CD34 to couple to IgG FcRs. After 4 h, the solution surrounding the scaffold is drawn off and replaced with DPBS and incubated for 30 min at 37° C. in a heating block. This buffer-exchange is repeated three times to afford the α-CD34-conjugated scaffold in DPBS.

Example 21

Scaffold from Cross-Linking PEG-OVS/PEG-OAm Microparticles Retaining Growth Factors for Release VS-OAm microparticles are fabricated as detailed in Example 6. VEGF is incorporated in poly(lactic/glycolic acid) microparticles using a double emulsion method known in the art. The two types of microparticles are mixed in DPBS.

This solution of microparticles is buffer-exchanged twice by: (1) adding triple the volume of DPBS of the microparticle solution and pipetting up and down to mix well, (2) centrifuging at 14,100 g for 2 min, (3) removing the supernatant, and (4) repeating steps 1-3.

The resuspended microparticles are gently shaken for 2 h in a temperature-controlled room at 37° C., centrifuged at 1000 g, and then incubated at 37° C. in a heating block overnight to afford a scaffold.

Example 22

Scaffold with Microparticles Retaining Lipids for Release

VS-BSA microparticles as in Example 8, but were formed from BSA incubated with 1 nmol S1P/mg BSA prior to pre-reaction. The solution of microparticles is buffer-exchanged twice by: (1) adding triple the volume of DPBS of the microparticle solution and pipetting up and down to mix well, (2) centrifuging at 14,100 g for 2 min, (3) removing the supernatant, and (4) repeating steps 1-3. Scaffolds were fabricated as detailed above using S1P-loaded VS-BSA microparticles.

Example 23

Gradients Formed by Density Difference

Figure 13:
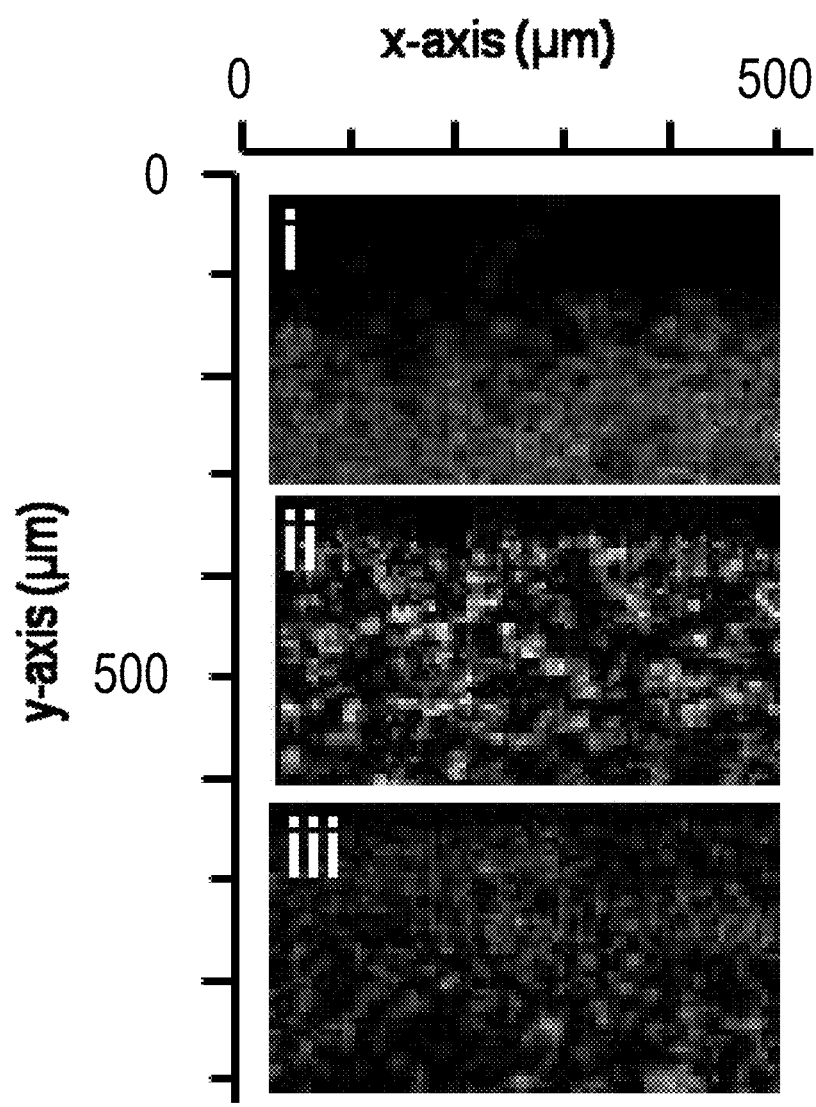
FIG. 13 presents gradient scaffolds formed by varying microparticle cross-linking density. Gradient scaffolds were formed by centrifuging standard OVS-BSA microparticles (white) with (i) low, (ii) medium or (iii) high density Ac-OAm microparticles (black). The density of the OAc-OAm microparticles was varied by reacting solutions of PEG-OAc and PEG-OAm in PBS+0.45 M sodium sulfate at 95° C. for: (i) 3 min, (ii) 5 min or (iii) 10 min.

Microparticles (VS-BSA & OAc-OAm) were formed as in Example 8 and Example 7, respectively. The density of the OAc-OAm microparticles was varied by reacting solutions of PEG-OAc and PEG-OAm in PBS+0.45 M sodium sulfate at 95° C. for: (i) 3 min, (ii) 5 min or (iii) 10 min. Gradient scaffolds were formed by centrifuging OVS-BSA microparticles with (i) low, (ii) medium or (iii) high density Ac-OAm microparticles (see FIG. 13).

Example 24

Gradients in Mechanical Properties

Microparticles are formed as in Example 6 (VS-OAm), except microparticles are independently formed with PEG-OVS of the following molecular weights: 10,000, 20,000 and 40,000. VS-OAm microparticles are washed 3× in DPBS. Microparticles formed from PEG-OVS 40,000 are added to an Eppendorf tube and allowed to settle. A solution containing PEG-OVS 20,000 microparticles is gently layered on top and allowed to settle, which is then repeated with PEG-OVS 10,000. The microparticles are cross-linked into scaffolds as above. The mechanical properties as a function of distance are measured by microindentation.

Example 25

Gradients Formed by Free Solution Electrophoresis

Microparticles (VS-OAm & TAc-OAm) are formed as in Example 6 and Example 2, respectively. The VS-OAm microparticles are reacted with an excess of succinic anhydride to convert positively charged amine groups to negatively charged carboxylic acid groups. The negatively charged microparticles are mixed with positively charged microparticles in a rectangular chamber containing electrodes at either end. The microparticles are subjected to free solution electrophoresis by application of 50 V, 50 mA across the chamber for 60 min. After settling, the microparticles are cross-linked in the presence of cross-linking peptide as above. After dissolution of the TA-OA microparticles overnight, the porosity of the scaffolds as a function of distance is measured by cryosectioning the scaffolds.

Example 26

Generic 3D Tissue Culture System

PEG-OVS/PEG-OAm microparticles were synthesized as detailed in Example 6. VS-OAm microparticles were fabricated in wells of a sterile tissue-culture polystyrene (TCPS) 24-well plate by diluting PEG-OVS/PEG-OAm microparticles 10× (final concentrations of 10 mg/mL for each reagent) with 1.5 M sodium sulfate in DPBS at pH 7.4, 20 mM RGD peptide solution in deionized water, and DPBS alone such that the final concentrations of sodium sulfate and RGD peptide were 600 mM and 200 µM respectfully, mixing well, and then incubating these for 24 h in a cell-culture incubator at 37° C. to afford a scaffold.

Example 27

Seeding Cells in the Scaffolds

Figure 14A:
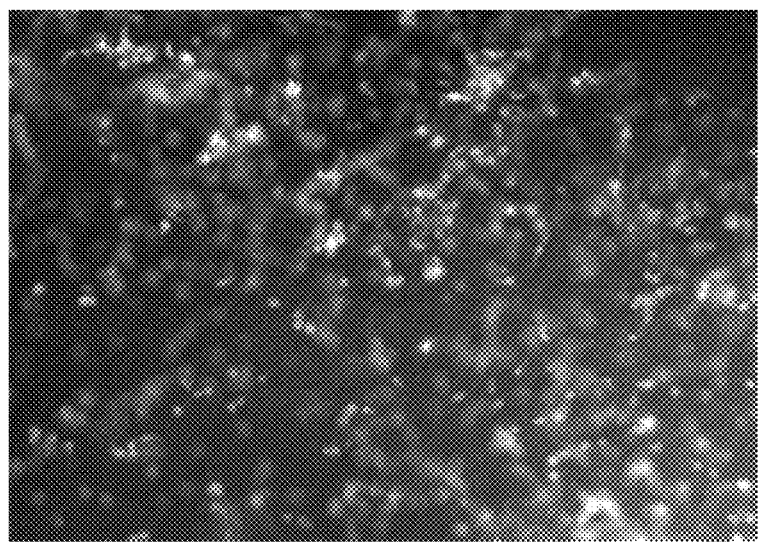
FIGS. 14A and 14B present fluorescence microscopy (10×) of scaffolds with (14A) and without (14B) conjugated RGD peptide in the presence of fibroblasts. Scaffolds were fabricated by allowing OVS-OAm microparticles to form in 600 mM sodium sulfate at 37° C. overnight. RGD conjugation was achieved by the addition of 5.5 mM peptide (Am-GCGYGRGDSPG) during microparticle formation. Scaffolds were buffer exchanged into media containing 2% serum and $2.5 \times 10^5$ fibroblasts/cm². Live cells were stained with fluorescein diacetate (white) after an overnight incubation at 37 C and washing with fresh media.
Figure 14B:
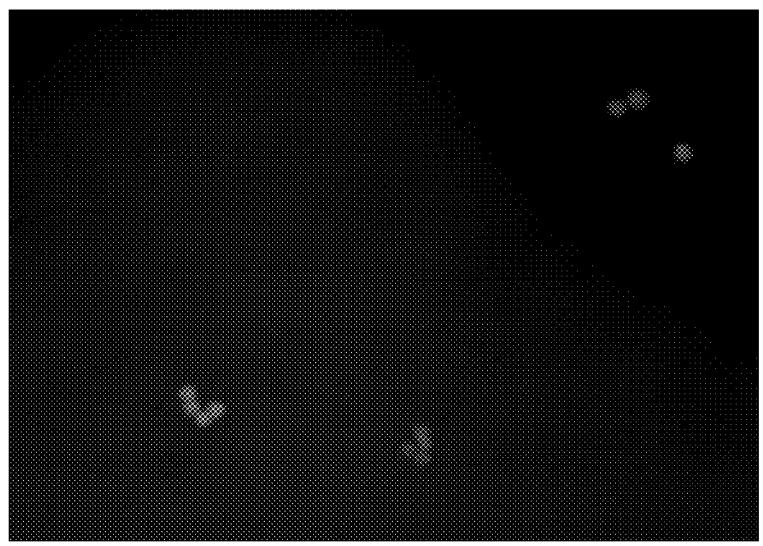

Scaffolds were formed as detailed in Example 26 and seeded with human fibroblast cells in vitro. Fibroblasts were cultured using an appropriate standard protocol and seeded at $2.5 \times 10^5$ cells/cm$^2$. Cell adhesion was assessed at 18 h using fluorescein diacetate to fluorescently label live cells. A photomicrograph of fibroblasts adhered to an RGD-conjugated scaffold fabricated using this protocol is shown in FIGS. 14A and 14B.

Example 28

In Vivo Induction of Angiogenesis Using Multiple Types of Microparticles to Form Scaffolds Microparticles (VS-OAm & TAc-OAm) are formed as in Example 6 and Example 2, respectively, and are mixed with microparticles containing VEGF as in Example 21. VS-BSA microparticles containing sphingosine 1-phosphate as in Example 22, and microparticles containing an antibody against CD34 as in Example 20. Scaffolds are formed, which are then implanted subcutaneously in the mouse. Angiogenesis is assessed after 7 days by sectioning the scaffolds on a cryostat and staining cells with Hematoxylin & Eosin.

Example 29

In Vivo Induction of Angiogenesis with a Hepatocyte Cell Line in the Scaffold

Scaffolds are formed as in Example 28, except that HepG2 hepatoma cells are added to the microparticles prior to scaffold formation. Survival of the HepG2 cells is assessed along with angiogenesis after 7 days subcutaneous implantation in the mouse. Angiogenesis is assessed after 7 days by sectioning the scaffolds on a cryostat and staining cells with Hematoxylin & Eosin.

Example 30

Substrate Coating to Reduce Protein Adsorption and Cell Adhesion from PEG-OVS/PEG-OA PEG-OVS/PEG-OAm microparticles are synthesized as in Example 6.

Oxygen-plasma cleaned glass coverslips are first solution-silanized with mercaptotrimethoxysilane (MPTS) by a 1 h incubation in 5% (v/v) MPTS in acetone followed by curing for 1 h at 100° C. MPTS-functionalized coverslips are then either used immediately or stored under nitrogen until use to minimize thiol oxidation.

Silanized coverslips are placed into wells of a 24-well plate made of tissue culture polystyrene and covered with a well-mixed solution of PEG-OVS/PEG-OAm microparticles diluted 10× (final concentrations of 10 mg/mL for each reagent) with 1.5 M sodium sulfate in Dulbecco's modified phosphate-buffered saline (DPBS; 8 mM sodium phosphate, 2 mM potassium phosphate, 140 mM sodium chloride, 10 mM potassium chloride) at pH 7.4 and DPBS alone such that the final concentration of sodium sulfate is 600 mM. The 24-well plate is then incubated at 37° C. for 120 min to coat the surface, and then it is washed 2× with and stored in DPBS.

Example 31

Precipitation Polymerization of PEG-Diacrylate

PEG-diacrylate, molecular weight 3400 (Sigma, St. Louis, Mo.) was dissolved in DPBS at 100 mg/mL. To this solution was added N-vinylpyrollidone (3.5 microL/mL), triethanolamine (115 mM) and Eosin Y (0.1 mM). Sodium sulfate was added at 700 mM. Photopolymerization was accomplished with a filtered lamp producing 100-150 mW of light between 480 and 520 nm (ILC Technology, Sunnyvale, Calif.) at 75 mW/cm$^2$ for 2 min at 25° C. or 37° C.

Figure 15A:
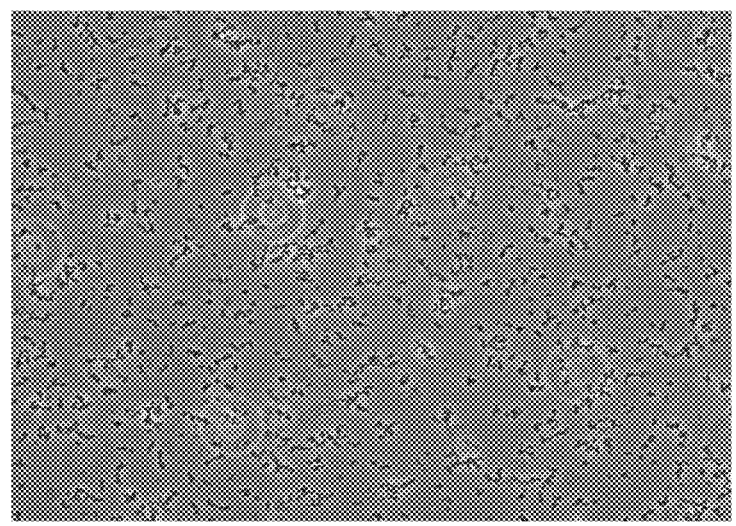
FIGS. 15A and 15B present microparticles formed by photopolymerization of PEG-diacrylate mol. wt. 3400 in 700 mM sodium sulfate. (15A) At 25° C., a monomodal size distribution results. (15B) At 37° C., bimodal size distribution results.
Figure 15B:
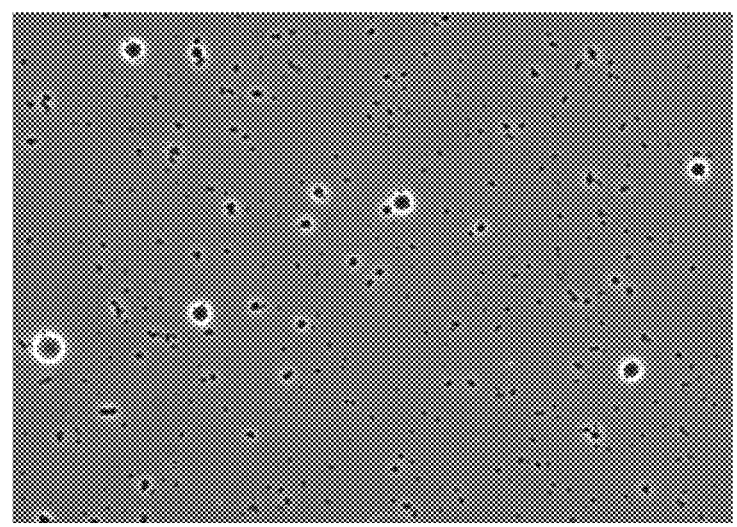
Figure 16:
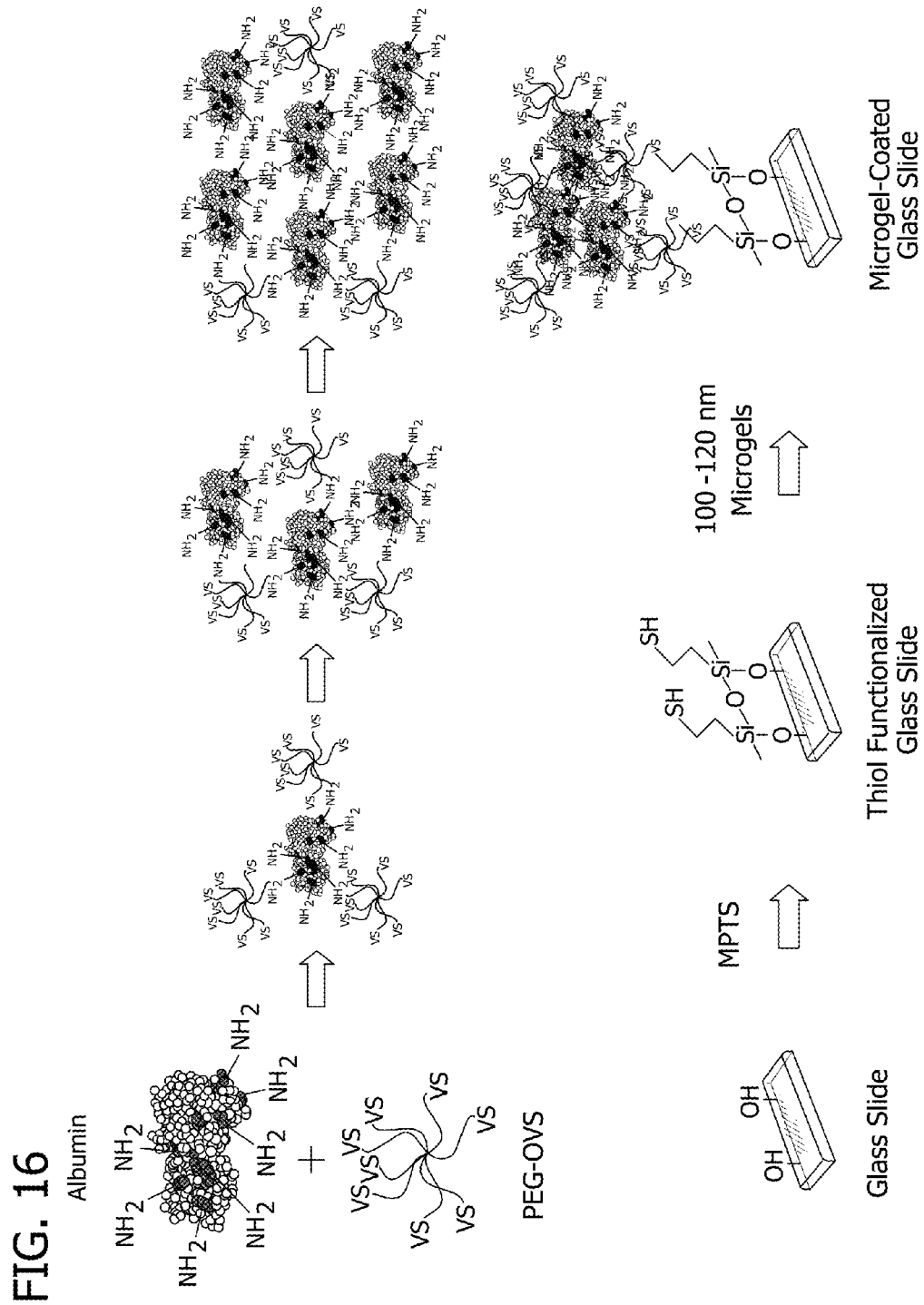
FIG. 16 presents a schematic showing the cross-linking and growth of PEG-OVS/BSA microparticles and their subsequent attachment to thiol-functionalized surfaces. Vinyl-sulfone groups on PEG molecules undergo a Michael-type addition with solvent-exposed and sterically accessible lysines on BSA, forming covalent linkages at neutral pH. If the cross-linking reaction is slowed before the gel point by dilution, microparticle-containing solutions can be rapidly reacted with nucleophile-derivatized surfaces, such as thiol-silanized glass, without detectable changes in microparticle size.
Figure 17:
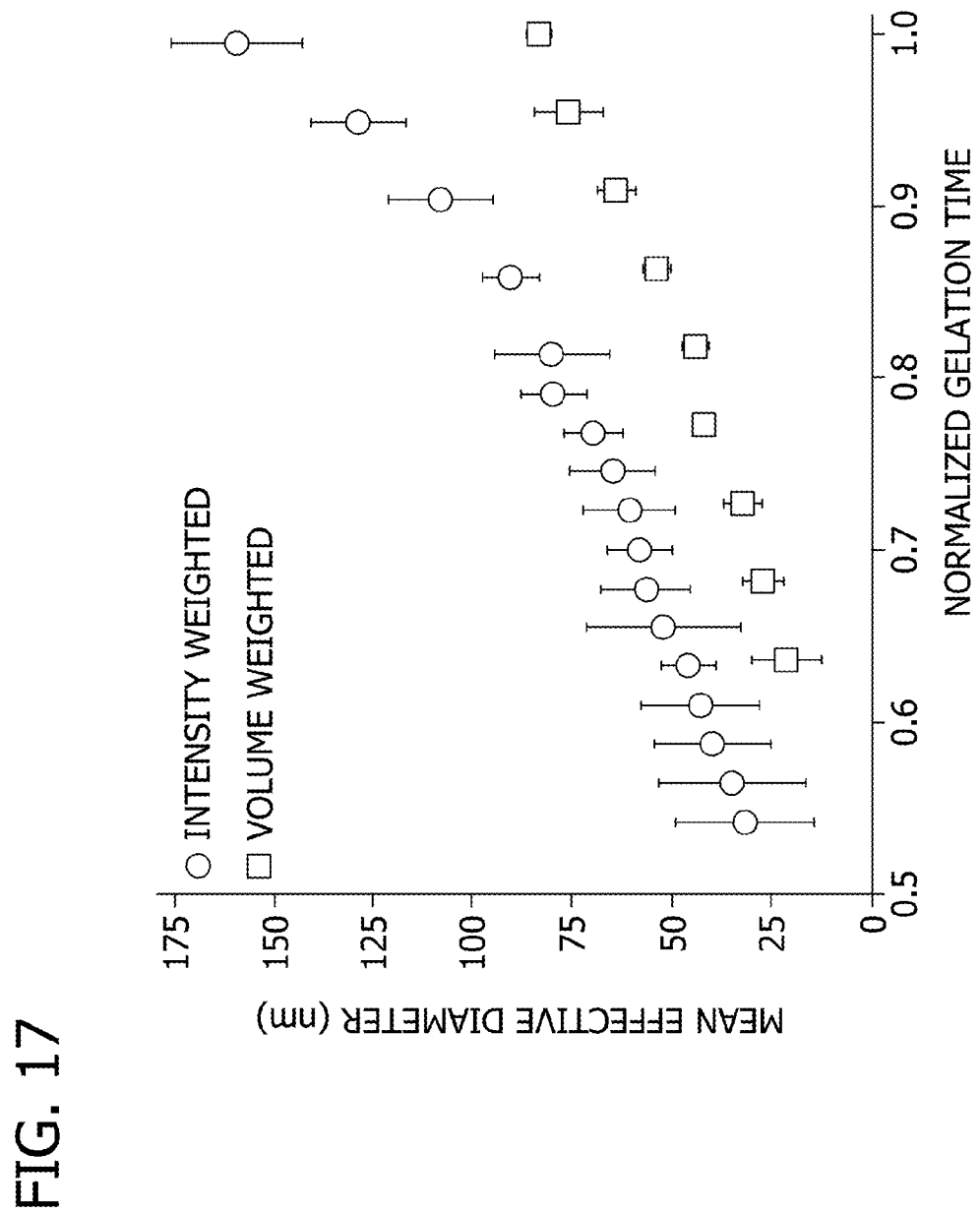
FIG. 17 presents intensity-weighted ($d_{PCS}$) and volume-weighted mean effective diameters of reacting PEG-OVS/BSA solutions (0.4:1 ratio of BSA amine groups to PEG vinylsulfone groups, 44 h gel time) measured with dynamic light scattering (DLS). The time scale was normalized relative to the time of gelation and error bars display the standard deviations for 4 separate reactions.
Figure 18:
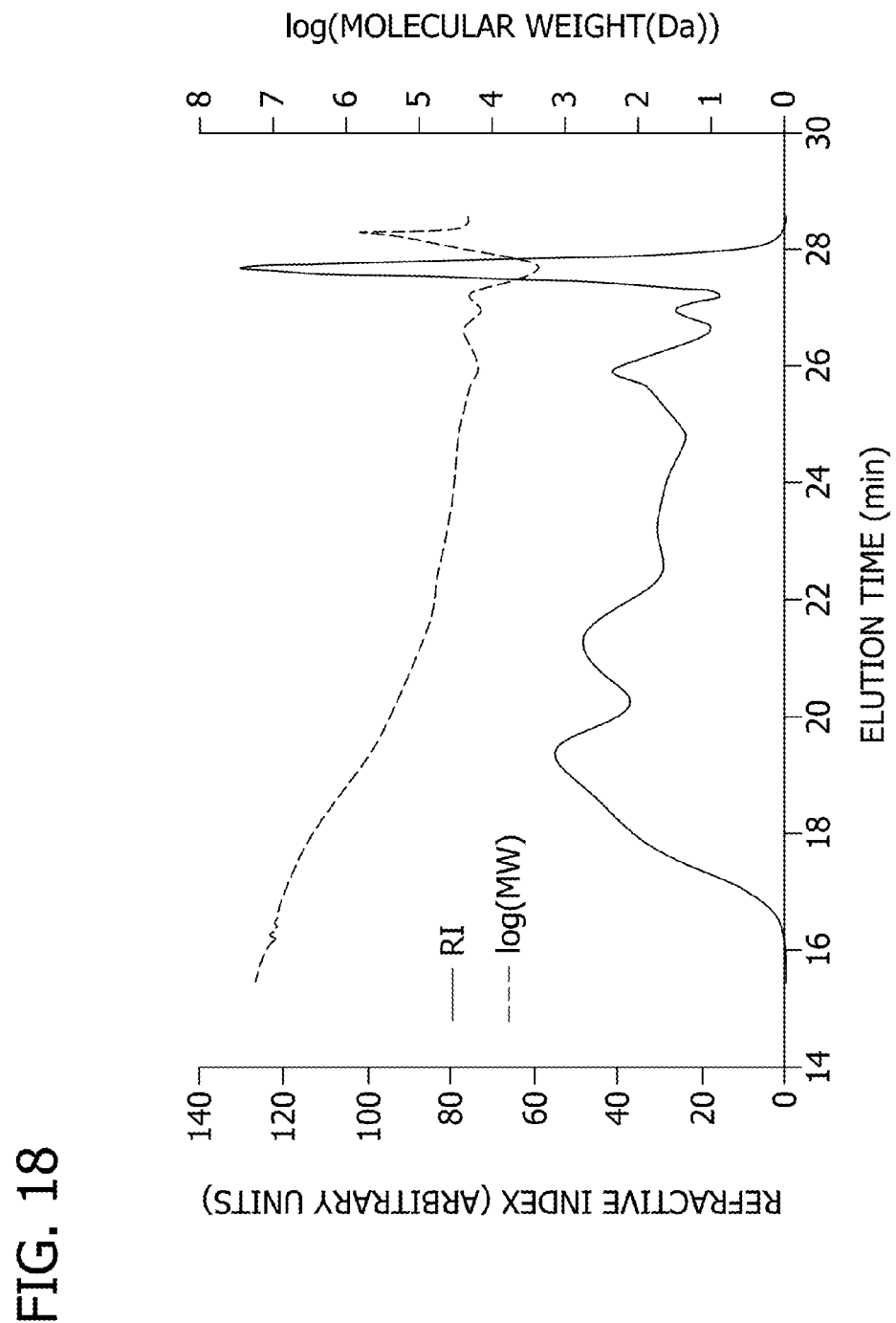
FIG. 18 presents a gel permeation chromatography (GPC) analysis of PEG-OVS/PEG-amine solutions pre-reacted to $d_{PCS} \cong 100$ nm. The reaction was halted by capping remaining vinylsulfone groups with 2-mercaptoethanol. Molecular weight (dashed line) and refractive index (bold line) of eluted polymers were plotted verses the elution time from a series of three PolyAnalytik High Resolution Aqueous Columns. The peak at 37.4 min was confirmed to be monomeric vinylsulfone in a separate run.
Figure 19:
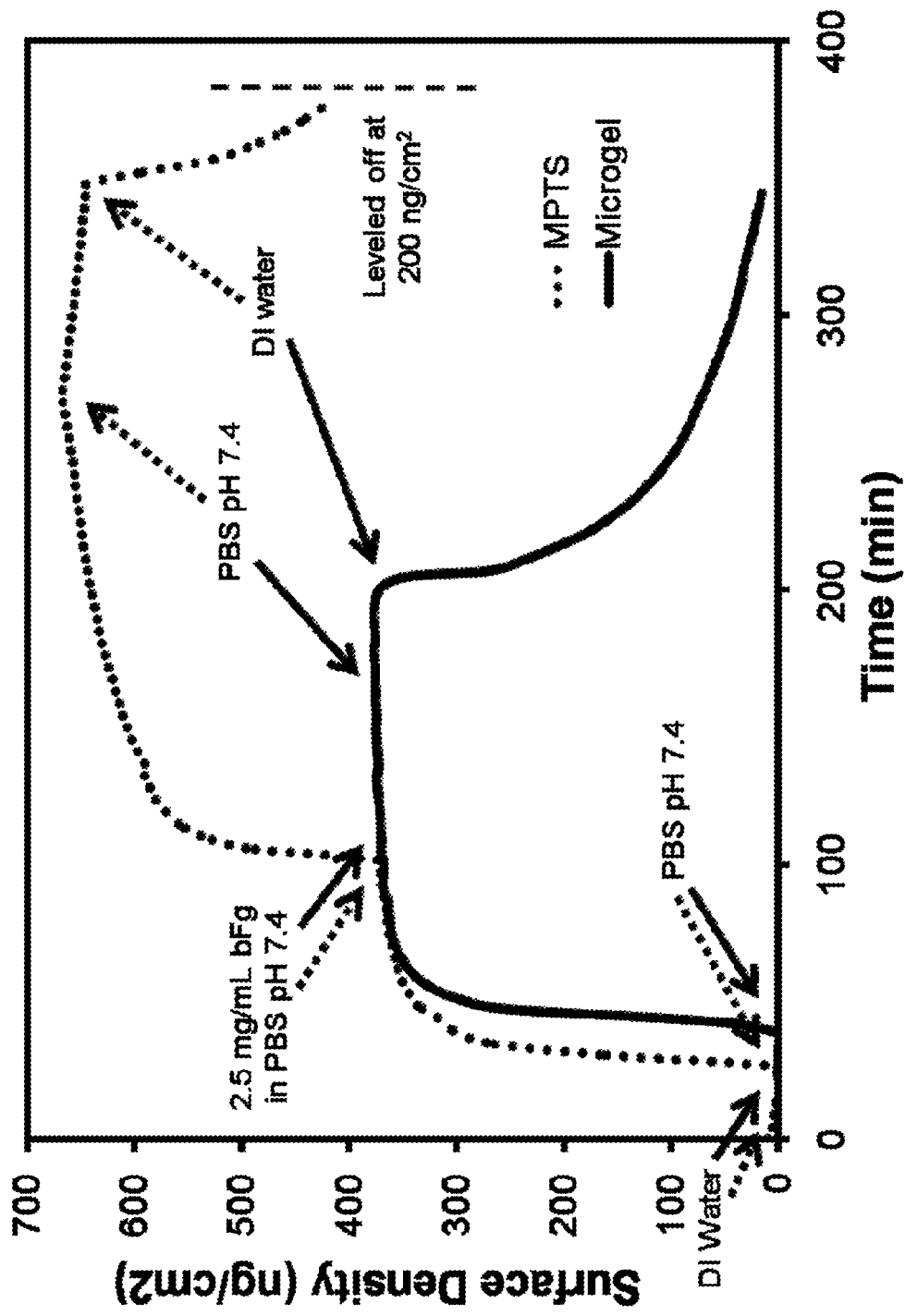
FIG. 19 presents an optical waveguide lightmode spectroscopy (OWLS) analysis of bovine fibrinogen (2.5 mg/mL in PBS) adsorption to microparticle-coated surfaces. Si/Ti/O$_2$ surfaces of OWLS waveguide chips were oxygen-plasma etched, vapor-silanized with MPTS, and incubated with PEG-OVS/BSA microparticles ($d_{PCS}$=100-120 nm). All surfaces were exposed to the same series of solutions flowing at 0.1 mL/min at 37° C.: (1) DI water, (2) PBS pH 7.4, (3) 2.5 mg/mL or 20 mg/mL bovine fibrinogen in PBS pH 7.4, (4) wash with PBS, pH 7.4, and (4) wash with DI water.
Figure 20:
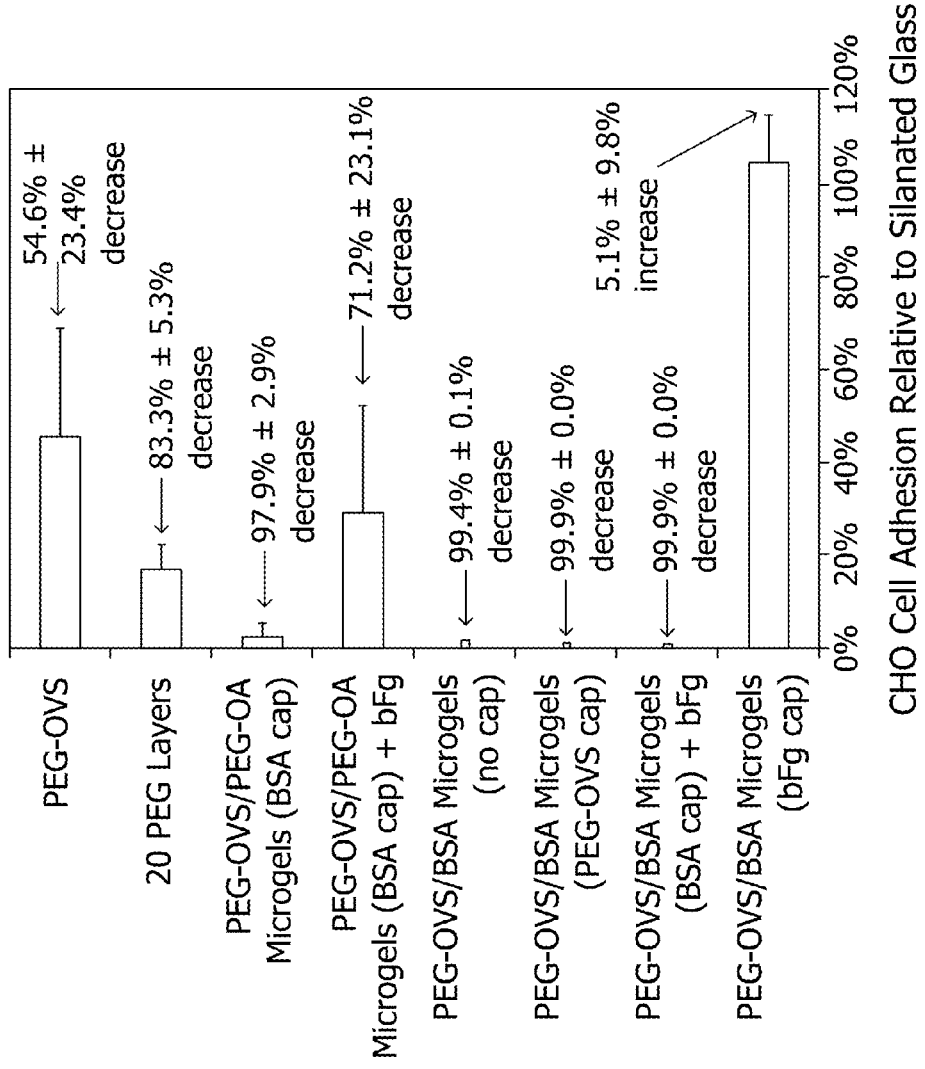
FIG. 20 presents cell counting data quantifying the adhesion of CHO cells to MPTS-silanized glass reacted with: (in order from top to bottom): (1) 100 mg/mL PEG-OVS in PBS; (2) 20 PEG-OVS layers alternating with DTT applied using a layer-by-layer method; (3-4) PEG-OVS/PEG-OA microparticles ($d_{PCS}$=100-120 nm) capped with (3) BSA; (4) BSA then incubated with bFg for 2 h; (5-8) PEG-OVS/BSA microparticles ($d_{PCS}$=100-120 nm) that were capped with: (5) PEG-OVS, (6) BSA, (7) BSA, then incubated with bFg for 2 h, or (8) bFg. CHO cells were seeded at a density of 2.5×10$^5$ cells/cm$^2$ and incubated with the surfaces for 24 h at 37° C.
Figures 21A, 21B, 21C, 21D:
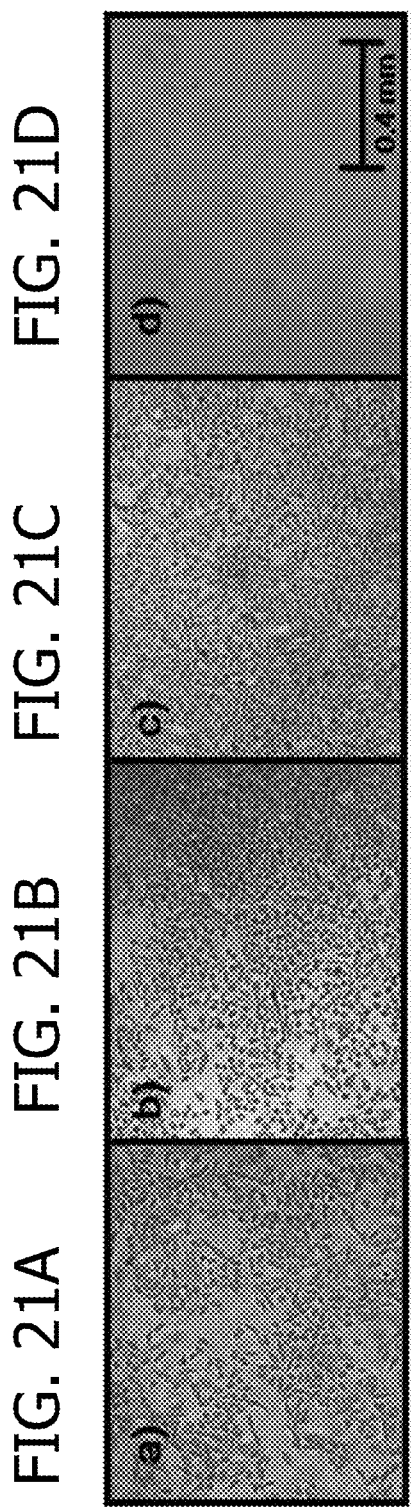
FIGS. 21A-21D present phase-contrast photomicrographs (10×) of CHO cell adhesion to air RFGD-treated PET films that were incubated for 24 h with: (21A) PBS, (21B) BSA, (21C) PEG-OVS, or (21D) PEG-OVS/BSA microparticles ($d_{PCS}$=100-120 nm) prior to incubation with 2.5×10$^5$ cells/cm$^2$.

The solutions photopolymerized at room temperature showed a monomodal distribution of microparticle sizes, while solutions photopolymerized at 37° C. showed a bimodal distribution of sizes (see FIGS. 15A and 15B).

Example 32

Characterization of Microparticle Formation During Reaction Below the Cloud Point Partially cross-linked microparticle-containing solutions with mean effective diameters between 30-160 nm by dynamic light scattering were formed by the cross-linking of poly(ethylene glycol)-octavinylsulfone with amine groups of either poly(ethylene glycol)-octaamine or bovine serum albumin below the cloud point of both polymers, as in Examples 1 and 3, respectively.

Methods.

Unless otherwise noted, all reagents were purchased from Sigma Aldrich (St. Louis, Mo.). Poly(ethylene glycol)-octavinylsulfone (PEG-OVS, 96% end-group conversion) and PEG-octaamine (PEG-OAm, 91% end-group conversion) were synthesized from 8-arm PEG-OH (mol wt 10,000, Shearwater Polymers, Huntsville, Ala.) as described in the art. PEG-OVS, PEG-OAm, and bovine serum albumin (BSA) solutions were prepared at 200 mg/mL in phosphate buffered saline (PBS; 0.2 g/L KCl, 0.2 g/L $KH_2PO_4$, 8 g/L NaCl, 1.15 g/L anhydrous $Na_2HPO_4$, pH 7.4) and sterile filtered with 0.22 µm sterile syringe tip filters (Millipore Corp., Billerica, Mass.). PEG-OVS/BSA or PEG-OVS/PEG-OAm microparticles were formed through Michael-type conjugate addition reactions by respectively mixing PEG-OVS with either BSA or PEG-OAm solutions at 0.4:1 or 1:1 ratios of amine to vinylsulfone groups. Ratios were prepared assuming that 8 moles of accessible functional groups per mole of PEG-OVS or PEG-OAm were available and that bovine serum albumin had approximately 36 lysines sterically-accessible for reaction, as known in the art. Microparticle solutions were maintained at 37° C. and rotated at 40 RPM until the desired microparticle diameter was reached.

Mean effective hydrodynamic diameters ($d_{PCS}$) were determined by dynamic light scattering (DLS; 90Plus Particle Size Analyzer, Brookhaven Instruments, Holtsville, N.Y.) at a scattering angle of 90° and wavelength of 658 nm. Disposable polystyrene cuvettes (Brookhaven Instruments) were cleaned 1× with 95% ethanol and 2× with DI water prior to use. Microparticle samples (30 µL) were collected at regular intervals and diluted with PBS (3 mL) in cleaned cuvettes and analyzed at 25° C. Calculation of mean effective microparticle diameters and statistical analysis of the results were performed using Brookhaven Instruments Particle Sizing Software (version 2.34, Brookhaven Instruments).

Results.

Microparticles were detected by dynamic light scattering after combining 200 mg/mL solutions of either BSA or PEG-OAm with 200 mg/mL PEG-OVS at an amine to vinylsulfone ratio of 1:1. Additionally, PEG-OVS/BSA microparticles were formed at an amine to vinylsulfone ratio of 0.4:1. When rotated at 37° C., the 0.4:1 and the 1:1 ratio PEG-OVS/BSA solutions reached the gel point after 44.6±0.6 h and 7.0±0.5 h, respectively. PEG-OVS/PEG-OAm solutions mixed at a 1:1 ratio formed gels in 6.7±0.3 h. Regardless of the ratio used, an increase in PEG-OVS/BSA microparticle diameter with time was observed by dynamic light scattering (DLS) until gelation. PEG-OVS/BSA microparticles were not reliably detected by DLS until reaching a mean effective diameter of 31.6±4.5 nm, which occurred after approximately 50% of the total gelation time. The largest detectable PEG-OVS/BSA microparticle size prior to gelation was 159.3±16.5 nm.

Example 33

Covalent Attachment of Microparticles to Glass Surfaces

The PEG microparticle-containing solutions were covalently reacted with glass surfaces to form a thin coating. Dilution of microparticle solutions sufficiently slowed microparticle growth to allow reaction with nucleophile-functionalized surfaces without a detectable change in microparticle size. Thus, thiol-functionalized glass was incubated with dilute microparticle solutions to permit rapid attachment to surfaces within a timeframe that permitted minimal growth in microparticle diameter. To quench unreacted vinylsulfone groups on the surface of the covalently-attached hydrogels, surface coatings were capped by incubation with solutions of BSA or PEG-OAm.

Methods.

Round glass coverslips (12 mm dia., Ted Pella Inc., Redding, Calif.) were functionalized with mercaptopropyltrimethoxysilane (MPTS) for covalent reaction with unreacted vinylsulfone groups in the microparticles. Coverslips were cleaned by washing 3× in DI water and 3× in ethanol prior to oxygen-plasma etching, which was performed at 50% power for 10 min with a 40 kHz, 100 W plasma etcher (Femto model, Diener Electronic, Reading, Pa.). The hydroxylated coverslips were then washed 3× in acetone and reacted for 1 h at 25° C. with a 5% (v/v) solution of MPTS in acetone. Surfaces were washed 3× in acetone and cured for 1 h at 100° C. under nitrogen. MPTS coverslips were incubated for 1 h with microparticle solutions ($d_{PCS}$=100-120 nm), washed 3× in PBS, and incubated overnight with PBS, BSA (50 mg/mL), or bovine fibrinogen (bFg, 2.5 mg/mL) at 37° C. to respectively form non-capped, BSA-capped, or fibrinogen-capped microparticles.

Results.

The following steps were utilized to covalently attach microparticle coatings to glass: 1) oxygen-plasma etching, 2) silanization with mercaptopropyltrimethoxysilane (MPTS), 3) 1 h incubation with a dilute microparticle suspensions in PBS pH 7.4 at 37° C., and 4) overnight incubation with 50 mg/mL BSA. Microparticles with mean effective diameters ($d_{PCS}$) between 100-120 nm were the largest microparticles capable of reacting with the MPTS functionalized surfaces at a 1:1 dilution within 1 h without a noticeable increasing in size measured by DLS at the end of the reaction.

Example 34

Properties and Protein Adsorption Resistance of PEG-OVS/BSA Microparticle Coatings The microparticle coatings were characterized with optical waveguide lightmode spectroscopy (OWLS) and quartz crystal microbalance with dissipation (QCM-D), which respectively measure the solid and liquid components of highly hydrated layers. Additionally, OWLS provides an independent measurement of optical masses than can be used to increase confidence in viscoelastic QCM models.

Methods.

$Si/Ti/O_2$, MPTS-silanized, and BSA-capped PEG-OVS/BSA microparticle-coated OWLS waveguide chips were analyzed inside the flow chamber of a MicroVacuum OWLS 110 optical waveguide lightmode spectrometer (MicroVacuum Ltd). All experiments were performed at a flow rate of 0.1 mL/min at 37° C. and with a time step of 30 s. Waveguide surfaces were first equilibrated under DI water until a transverse magnetic mode refractive index variation of <1×10$^{-6}$ was obtained. For coating characterization at each step of the coating process, MPTS-silanized waveguide chips were coated with microparticle solutions in situ and tested for fibrinogen adsorption using the following sequence of flowing solutions: 1) DI water, 2) PBS, 3) 2 h incubation with PEG-OVS/BSA microparticle solutions ($d_{PCS}$=100-120 nm) in PBS, 4) PBS wash/equilibration, 5) overnight incubation with BSA in PBS, 6) PBS wash/equilibration, 7) 2 h incubation with 2.5 mg/mL bFg in PBS, 8) PBS wash/equilibration, and 9) DI water wash/equilibration. Waveguide chips precoated with BSA-capped PEG-OVS/BSA microparticles were analyzed specifically for fibrinogen adsorption using the following series of solutions: 1) DI water, 2) PBS, 3) 2 h incubation with 2.5 mg/mL or 20 mg/mL bFg in PBS, 4) PBS wash/equilibration, and 5) DI water wash/equilibration.

Results.

The optical mass and protein adsorption resistance of microparticle coatings was quantified with OWLS. Since it is known that OWLS has an upper limit of sensitivity above the waveguide surface, vapor silanization was employed instead of solution silanization, to limit silane aggregation and thickness. Solutions of PEG-OVS/BSA microparticles ($d_{PCS}$=100-120 nm) were flowed over Si/Ti/O$_2$ or MPTS waveguide surfaces, resulting in surface mass densities of 115.0±0.7 ng/cm$^2$ and 267.38±8.58 ng/cm$^2$, respectively.

Resistance to protein adsorption was tested by comparing the adsorption of bovine fibrinogen (bFg) on MPTS surfaces to BSA-capped PEG-OVS/BSA microparticle-coated surfaces. While bFg readily adsorbed to the MPTS surface at 201.9±1.2 ng/cm$^2$, no detectable change in refractive index was observed for the microparticle surface when switching from the PBS solution to the 2.5 mg/mL bFg solution in PBS (see FIG. 8). To verify that the microparticle coated OWLS waveguide chip was still sensitive to refractive index changes above the microparticle surface, the adsorption experiment was repeated with an 8-fold higher concentration of bFg. The refractive index of the 20 mg/mL bFg solution was verified with a refractometer to be 0.0042 higher than PBS alone, and this difference in refractive index was detected by OWLS when switching from PBS to 20 mg/mL bFg in PBS on the microparticle surface (see FIG. 9). After switching the solution back to PBS and DI water for washing, only 4.1±0.9 ng/cm$^2$ of bFg was detected in comparison to 192±3.3 ng/cm$^2$ on the MPTS surface under the same conditions.

QCM was utilized to monitor PEG attachment to MPTS surfaces. Quartz sensors were silanized in solution with MPTS prior to QCM analysis. Microparticle coatings were formed on the surfaces using the same protocol as for glass slides, including the final capping step with BSA. Incubations with microparticle suspensions ($d_{PCS}$=100-120 nm), BSA solutions, and bFg solutions were all performed within the QCM itself. Comparison between the optical mass and Voight mass for PEG-OVS/BSA microparticles revealed the presence of a highly hydrated coating that was ~97% water. After capping with BSA, the water content was ~93%. Although $d_{PCS}$=100 nm diameter microparticle solutions were grafted to surfaces, the microparticle coating thickness was estimated to be only ~75 nm.

Example 35

Resistance of Microparticle Coated Glass to Cell Adhesion

Glass slides were coated with microparticles and incubated with Chinese hamster ovary (CHO), fibroblast, or endothelial cells to test for resistance to cell adhesion and spreading.

Methods.

CHO cells (ATCC, Manassas, Va.), human aortic endothelial cells (HAEC; Lonza, Walkersville, Md.), and 3T3 fibroblasts were maintained using standard cell culture protocols specific to each cell line. Microparticle-coated coverslips were placed into 24-well plates of tissue-culture polystyrene (Becton Dickinson Labware, Franklin Lakes, N.J.) and washed 3× with PBS and 1× with the appropriate cell media. Wells were seeded with cells at 2.5×10$^5$ cells/cm$^2$ and incubated for 12 h at 37° C. After incubation, surfaces were washed 3× with media and cell adhesion was assessed by phase contrast microscopy. Photomicrographs were taken at 10× magnification and the number of attached cells was counted manually. The cell adhesion experiments were modified slightly for the long-term fibroblast reseeding experiments. Surfaces were washed and seeded with 2.5×10$^5$ cells/cm$^2$ every 48 h and observed by microscopy every 24 h. Microscopy was performed on unwashed surfaces to observe the aggregation of non-adherent fibroblasts in solution.

Results.

All cells adhered to and spread on MPTS surfaces and BSA-coated MPTS surfaces during the 24 h incubation period. While fewer cells adhered to the PEG-OVS grafted surfaces, no spread cells and few adhered cells were found on the microparticle coated surfaces. Long-term resistance to fibroblast adhesion was tested for BSA-capped PEG-OVS/BSA microparticles reacted with silanized and non-silanized surfaces by reseeding fresh cells onto surfaces every 2 days. Non-adherent fibroblasts were observed to clump into aggregates above the surfaces, as MPTS glass surfaces coated with BSA-capped PEG-OVS/BSA microparticles resisted cell adhesion for up to 19 days. In contrast, extensive fibroblast adhesion was observed on non-silanized glass surfaces after the first day of incubation. Capping the microparticles with BSA resulted in a small decrease in cell adhesion compared to uncapped microparticles. PEG-OVS/PEG-OA gels capped with BSA displayed slightly more cell adhesion that PEG-OVS/BSA gels capped with BSA, but the difference was also not statistically significant. The resistance of BSA-capped PEG-OVS/BSA microparticles to CHO and fibroblast adhesion was not influenced by preincubation with a fibrinogen solution immediately prior to cell seeding. BSA-capped PEG-OVS/PEG-OA microparticles were not as resistant to cell adhesion as BSA-capped PEG-OVS/BSA microparticles after incubation with fibrinogen solutions. Cell adhesion to PEG-OVS/BSA microparticles was promoted when a bovine fibrinogen cap was used instead of a BSA cap, suggesting the presence of reactive vinylsulfone groups in the coating. Compared to gels formed with a covalent layer-by-layer method known in the art, the microparticles were superior in preventing cell adhesion.

Example 36

Application of Microparticle Coating to PET Surfaces

Microparticle coatings were applied to poly(ethylene terephthalate) PET surfaces and tested for cell adhesion.

Methods.

Poly(ethylene terephthalate) films (PET, 0.05 mm thick, McMaster Carr, Chicago, Ill.) were functionalized with air-plasma prior to coating with microparticles. Circular sections (12 mm dia.) were cut from PET sheets and washed 3× in DI water and ethanol prior to radio frequency glow discharge air plasma (RFGD) treatments for 10 min at 50% power. Air-plasma etched PET (RFGD-PET) surfaces were incubated with 1:3 dilutions of microparticles ($d_{PCS}$=40-50 nm) in PBS for 12 h. Coated RFGD-PET was washed and stored in PBS until use.

Results.

Microparticle coatings were applied to PET surfaces using a 2-step process. The first step was etching of the surface with air-plasma to provide a low surface density of amine groups. The second step was incubation with 1:3 dilutions of BSA/PEG microparticles ($d_{PCS}$=40.1±0.99 nm) for 12 h. A longer incubation time was utilized compared to the microparticle coating of thiol-functionalized surfaces due to the slower reaction kinetics between vinylsulfone and primary amines. The smaller diameter microparticles and a more dilute microparticle solution were used to limit microparticle growth over the 12 h incubation. Microparticle solution mean effective diameters were found by DLS to still be below 100 nm after the longer incubation period. Even without the capping step, microparticle coatings on RFGD-PET demonstrated considerable resistance to CHO cell adhesion (2.3±3.2 adhered cells/mm$^2$) compared to RFGD-PET (1100±216 cells/mm$^2$), BSA-adsorbed RFGD-PET (850±129 cells/mm$^2$) and PEG-OVS grafted RFGD-PET (975±95 cells/mm$^2$).

What is claimed is:

1. A process for forming microparticles comprising a cross-linked water-soluble polymer or cross-linked water-soluble polymers; the process comprising:
   combining macromers comprising at least one water-soluble polymer and at least one cross-linking agent in an aqueous solvent, wherein at least one of the macromers comprises a functionality of greater than 2, wherein at least one of the water-soluble polymers comprises a lower critical solution temperature (LCST), wherein functional groups of the cross-linking agent and the macromers react to form covalent bonds, wherein the covalent bonds form the cross-linked water-soluble polymer; and
   coacervation polymerizing the macromers to form a solution, wherein the coacervation polymerization comprises cross-linking the macromers at a temperature that is above the lower critical solution temperature (LCST) of at least one of the macromers, wherein the coacervation polymerization is done in the absence of mixing or agitation, wherein polymer-rich phases of the cross-linked water-soluble polymers gel before the solution coarsens to form droplets less than about 1 mm in diameter, wherein the macromers comprises at least one water-soluble polymer selected from the group consisting of polyacrylate, polyacrylamide, poly(acrylamide sulphonic acid), polyacrylonitrile, polyamines, poly(ethylene glycol), poly(ethylene imine), poly(ethylene oxide), poly(ethyloxazoline), polyhydroxyethylacrylate, polymethacrylate, polymethacrylamide, poly(oxyalkylene oxide), poly(propylene oxide), polyurethane, poly(vinyl alcohol), and poly(vinyl pyrrolidone).

2. The process for forming microparticles as set forth in claim 1, further comprising polymerizing the macromers before heating the macromers above the LCST of the macromers.

3. The process for forming microparticles as set forth in claim 1, wherein the macromers comprise greater than about 75% by weight poly(ethylene glycol) or poly(vinyl pyrrolidone).

4. The process for forming microparticles as set forth in claim 1, wherein the process is free of a surfactant or a solvent other than water.

5. The process for forming microparticles as set forth in claim 1, wherein the cross-linking agent is selected from the group consisting of a small molecule, a peptide, a protein, a linker molecule, a biomolecule, and macromers of a water-soluble polymer.

6. The process for forming microparticles as set forth in claim 1, wherein the polymerization is a condensation polymerization.

7. The process for forming microparticles as set forth in claim 1, wherein the covalent bonds formed by the reaction between the macromers and the cross-linking agent are essentially non-degradable, degradable by hydrolysis, or enzymatically degradable.

8. The process for forming microparticles as set forth in claim 1, further comprising decreasing the LCST of the water-soluble polymers, wherein the LCST is decreased by increasing a concentration of ions in the solvent.

9. The process for forming microparticles as set forth in claim 1, further comprising including therapeutic molecules in the microparticles via affinity interactions.

10. A process for forming a coating on a surface, wherein the surface comprises microparticles of a cross-linked water-soluble polymer, the process comprising:
    combining macromers comprising at least one water-soluble polymer and at least one cross-linking agent in an aqueous solvent, wherein at least one of the macromers comprises a functionality of greater than 2, wherein at least one of the water-soluble polymers comprises a lower critical solution temperature (LCST), wherein functional groups of the cross-linking agent and the macromers react to form covalent bonds, wherein the covalent bonds form the cross-linked water-soluble polymer;
    coacervation polymerizing the macromers to form a solution, wherein the coacervation polymerization comprises cross-linking the macromers at a temperature that is above the lower critical solution temperature (LCST) of at least one of the macromers, wherein the coacervation polymerization is done in the absence of mixing or agitation, wherein polymer-rich phases of the cross-linked water-soluble polymers gel before the solution coarsens to form droplets less than about 1 mm in diameter; and
    forming the coating by contacting a solution of the microparticle with the surface, wherein the surface is derivatized with functional groups that react with microparticle functional groups, wherein the macromers comprises at least one water-soluble polymer selected from the group consisting of polyacrylate, polyacrylamide, poly(acrylamide sulphonic acid), polyacrylonitrile, polyamines, poly(ethylene glycol), poly(ethylene imine), poly(ethylene oxide), poly(ethyloxazoline), polyhydroxyethylacrylate, polymethacrylate, polymethacrylamide, poly(oxyalkylene oxide), poly(propylene oxide), polyurethane, poly(vinyl alcohol), and poly(vinyl pyrrolidone).

11. The process for forming a coating as set forth in claim 10, wherein the surface is a medical device selected from the group consisting of a cardiovascular device, an artificial blood vessel, an artificial bone joint, a biosensor, a scaffold that supports tissue or cell growth, and a percutaneous device.

12. The process for forming a coating as set forth in claim 10, wherein the coating has a thickness that is less than about 10 microns.

13. The process for forming a coating as set forth in claim 10, wherein the surface is from about 90 percent to about 99 percent protein rejecting.

14. The process for forming a coating as set forth in claim 10, wherein the microparticle further comprises a non-covalently conjugated therapeutic molecule.

15. The process for forming a coating as set forth in claim 14, wherein the therapeutic molecule is selected from the group consisting of a small molecule, a pharmaceutically active agent, a lipid, a peptide, a protein, an enzyme, a growth factor, and an antibody.

16. The process for forming a coating as set forth in claim 10, wherein the surface is a material used for a diagnostic assay.

17. The process for forming a coating as set forth in claim 10, wherein the surface is glass.

18. The process for forming a coating as set forth in claim 15, wherein the microparticle comprises an antibody.

* * * * *